(12) United States Patent
Eldardiry et al.

(10) Patent No.: US 10,078,062 B2
(45) Date of Patent: Sep. 18, 2018

(54) DEVICE HEALTH ESTIMATION BY COMBINING CONTEXTUAL INFORMATION WITH SENSOR DATA

(71) Applicant: Palo Alto Research Center Incorporated, Palo Alto, CA (US)

(72) Inventors: Hoda M. A. Eldardiry, San Carlos, CA (US); Linxia Liao, Fremont, CA (US); Tomonori Honda, Redwood City, CA (US); Bhaskar Saha, Redwood City, CA (US); Rui Abreu, Sunnyvale, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 240 days.

(21) Appl. No.: 14/969,984

(22) Filed: Dec. 15, 2015

(65) Prior Publication Data
US 2017/0167993 A1 Jun. 15, 2017

(51) Int. Cl.
*G01N 25/72* (2006.01)
*G05B 13/00* (2006.01)

(52) U.S. Cl.
CPC ............ *G01N 25/72* (2013.01); *G05B 13/00* (2013.01)

(58) Field of Classification Search
CPC ................................ G01N 25/72; G05B 13/00
(Continued)

(56) References Cited

U.S. PATENT DOCUMENTS

| 817,441 A | 4/1906 | Niesz |
| 3,921,945 A * | 11/1975 | Swaim ................... B61F 9/005 188/110 |

(Continued)

FOREIGN PATENT DOCUMENTS

| DE | 1720277 A1 | 6/1967 |
| DE | 19620817 A1 | 11/1997 |

(Continued)

OTHER PUBLICATIONS

Jacobson, Van et al., "Content-Centric Networking, Whitepaper Describing Future Assurable Global Networks", Palo Alto Research Center, Inc., Jan. 30, 2007, pp. 1-9.

(Continued)

*Primary Examiner* — Bo Fan
(74) *Attorney, Agent, or Firm* — Shun Yao; Park, Vaughan, Fleming & Dowler LLP

(57) ABSTRACT

A method and system for detecting fault in a machine. During operation, the system obtains control signals and corresponding sensor data that indicates a condition of the machine. The system determines consistent time intervals for each of the control signals. During a consistent time interval the standard deviation of a respective control signal is less than a respective predetermined threshold. The system aggregates the consistent time intervals to determine aggregate consistent intervals. The system then maps the aggregate consistent intervals to the sensor data to determine time interval segments for the sensor data. The system may generate features based on the sensor data. Each respective feature is generated from a time interval segment of the sensor data. The system trains a classifier using the features, and applies the classifier to additional sensor data indicating a condition of the machine over a period of time to detect a machine fault.

20 Claims, 7 Drawing Sheets

(58) Field of Classification Search
USPC .......................................................... 702/132
See application file for complete search history.

(56) References Cited

U.S. PATENT DOCUMENTS

| | | | |
|---|---|---|---|
| 4,309,569 A | 1/1982 | Merkle | |
| 4,921,898 A | 5/1990 | Lenney | |
| 5,070,134 A | 12/1991 | Oyamada | |
| 5,110,856 A | 5/1992 | Oyamada | |
| 5,506,844 A | 4/1996 | Rao | |
| 5,629,370 A | 5/1997 | Freidzon | |
| 5,870,605 A | 2/1999 | Bracho | |
| 6,052,683 A | 4/2000 | Irwin | |
| 6,085,320 A | 7/2000 | Kaliski et al. | |
| 6,091,724 A | 7/2000 | Chandra | |
| 6,173,364 B1 | 1/2001 | Zenchelsky | |
| 6,226,618 B1 | 5/2001 | Downs | |
| 6,233,617 B1 | 5/2001 | Rothwein | |
| 6,233,646 B1 | 5/2001 | Hahm | |
| 6,332,158 B1 | 12/2001 | Risley | |
| 6,366,988 B1 | 4/2002 | Skiba | |
| 6,574,377 B1 | 6/2003 | Cahill | |
| 6,654,792 B1 | 11/2003 | Verma | |
| 6,667,957 B1 | 12/2003 | Corson | |
| 6,681,220 B1 | 1/2004 | Kaplan | |
| 6,681,326 B2 | 1/2004 | Son | |
| 6,769,066 B1 | 7/2004 | Botros | |
| 6,772,333 B1 | 8/2004 | Brendel | |
| 6,862,280 B1 | 3/2005 | Bertagna | |
| 6,901,452 B1 | 5/2005 | Bertagna | |
| 6,917,985 B2 | 7/2005 | Madruga | |
| 6,968,393 B1 | 11/2005 | Chen | |
| 6,981,029 B1 | 12/2005 | Menditto | |
| 7,013,389 B1 | 3/2006 | Srivastava | |
| 7,031,308 B2 | 4/2006 | Garcia-Luna-Aceves | |
| 7,061,877 B1 | 6/2006 | Gummalla | |
| 7,152,094 B1 | 12/2006 | Jannu | |
| 7,177,646 B2 | 2/2007 | ONeill | |
| 7,206,860 B2 | 4/2007 | Murakami | |
| 7,257,837 B2 | 8/2007 | Xu | |
| 7,287,275 B2 | 10/2007 | Moskowitz | |
| 7,315,541 B1 | 1/2008 | Housel | |
| 7,339,929 B2 | 3/2008 | Zelig | |
| 7,350,229 B1 | 3/2008 | Lander | |
| 7,362,727 B1 | 4/2008 | ONeill | |
| 7,382,787 B1 | 6/2008 | Barnes | |
| 7,430,755 B1 | 9/2008 | Hughes | |
| 7,444,251 B2 | 10/2008 | Nikovski | |
| 7,466,703 B1 | 12/2008 | Arunachalam | |
| 7,472,422 B1 | 12/2008 | Agbabian | |
| 7,496,668 B2 | 2/2009 | Hawkinson | |
| 7,509,425 B1 | 3/2009 | Rosenberg | |
| 7,523,016 B1 | 4/2009 | Surdulescu | |
| 7,542,471 B2 | 6/2009 | Samuels | |
| 7,543,064 B2 | 6/2009 | Juncker | |
| 7,552,233 B2 | 6/2009 | Raju | |
| 7,555,482 B2 | 6/2009 | Korkus | |
| 7,555,563 B2 | 6/2009 | Ott | |
| 7,564,812 B1 | 7/2009 | Elliott | |
| 7,567,547 B2 | 7/2009 | Mosko | |
| 7,567,946 B2 | 7/2009 | Andreoli | |
| 7,580,971 B1 | 8/2009 | Gollapudi | |
| 7,623,535 B2 | 11/2009 | Guichard | |
| 7,647,507 B1 | 1/2010 | Feng | |
| 7,660,324 B2 | 2/2010 | Oguchi | |
| 7,685,290 B2 | 3/2010 | Satapati | |
| 7,698,463 B2 | 4/2010 | Ogier | |
| 7,769,887 B1 | 8/2010 | Bhattacharyya | |
| 7,779,467 B2 | 8/2010 | Choi | |
| 7,801,177 B2 | 9/2010 | Luss | |
| 7,816,441 B2 | 10/2010 | Elizalde | |
| 7,831,733 B2 | 11/2010 | Sultan | |
| 7,908,337 B2 | 3/2011 | Garcia-Luna-Aceves | |
| 7,924,837 B1 | 4/2011 | Shabtay | |
| 7,953,885 B1 | 5/2011 | Devireddy | |
| 8,000,267 B2 | 8/2011 | Solis | |
| 8,010,691 B2 | 8/2011 | Kollmansberger | |
| 8,074,289 B1 | 12/2011 | Carpentier | |
| 8,117,441 B2 | 2/2012 | Kurien | |
| 8,160,069 B2 | 4/2012 | Jacobson | |
| 8,204,060 B2 | 6/2012 | Jacobson | |
| 8,214,364 B2 | 7/2012 | Bigus | |
| 8,224,985 B2 | 7/2012 | Takeda | |
| 8,225,057 B1 | 7/2012 | Zheng | |
| 8,271,578 B2 | 9/2012 | Sheffi | |
| 8,312,064 B1 | 11/2012 | Gauvin | |
| 8,386,622 B2 | 2/2013 | Jacobson | |
| 8,467,297 B2 | 6/2013 | Liu | |
| 8,473,633 B2 | 6/2013 | Eardley | |
| 8,553,562 B2 | 10/2013 | Allan | |
| 8,572,214 B2 | 10/2013 | Garcia-Luna-Aceves | |
| 8,654,649 B2 | 2/2014 | Vasseur | |
| 8,665,757 B2 | 3/2014 | Kling | |
| 8,667,172 B2 | 3/2014 | Ravindran | |
| 8,688,619 B1 | 4/2014 | Ezick | |
| 8,699,350 B1 | 4/2014 | Kumar | |
| 8,718,055 B2 | 5/2014 | Vasseur | |
| 8,750,820 B2 | 6/2014 | Allan | |
| 8,761,022 B2 | 6/2014 | Chiabaut | |
| 8,762,477 B2 | 6/2014 | Xie | |
| 8,762,570 B2 | 6/2014 | Qian | |
| 8,762,707 B2 | 6/2014 | Killian | |
| 8,767,627 B2 | 7/2014 | Ezure | |
| 8,817,594 B2 | 8/2014 | Gero | |
| 8,826,381 B2 | 9/2014 | Kim | |
| 8,832,302 B1 | 9/2014 | Bradford | |
| 8,836,536 B2 | 9/2014 | Marwah | |
| 8,862,774 B2 | 10/2014 | Vasseur | |
| 8,868,779 B2 | 10/2014 | ONeill | |
| 8,903,756 B2 | 12/2014 | Zhao | |
| 8,934,496 B2 | 1/2015 | Vasseur | |
| 8,937,865 B1 | 1/2015 | Kumar | |
| 9,071,498 B2 | 6/2015 | Beser | |
| 9,112,895 B1 | 8/2015 | Lin | |
| 2002/0010795 A1 | 1/2002 | Brown | |
| 2002/0038296 A1 | 3/2002 | Margolus | |
| 2002/0048269 A1 | 4/2002 | Hong | |
| 2002/0054593 A1 | 5/2002 | Morohashi | |
| 2002/0077988 A1 | 6/2002 | Sasaki | |
| 2002/0078066 A1 | 6/2002 | Robinson | |
| 2002/0138551 A1 | 9/2002 | Erickson | |
| 2002/0176404 A1 | 11/2002 | Girard | |
| 2002/0188605 A1 | 12/2002 | Adya | |
| 2002/0199014 A1 | 12/2002 | Yang | |
| 2003/0033394 A1 | 2/2003 | Stine | |
| 2003/0046437 A1 | 3/2003 | Eytchison | |
| 2003/0048793 A1 | 3/2003 | Pochon | |
| 2003/0051100 A1 | 3/2003 | Patel | |
| 2003/0074472 A1 | 4/2003 | Lucco | |
| 2003/0088696 A1 | 5/2003 | McCanne | |
| 2003/0097447 A1 | 5/2003 | Johnston | |
| 2003/0099237 A1 | 5/2003 | Mitra | |
| 2003/0140257 A1 | 7/2003 | Peterka | |
| 2003/0158694 A1* | 8/2003 | Wegerich | G01D 3/08 702/127 |
| 2003/0195688 A1* | 10/2003 | Mensler | F16H 61/6648 701/61 |
| 2003/0229892 A1 | 12/2003 | Sardera | |
| 2004/0024879 A1 | 2/2004 | Dingman | |
| 2004/0030602 A1 | 2/2004 | Rosenquist | |
| 2004/0071140 A1 | 4/2004 | Jason | |
| 2004/0073715 A1 | 4/2004 | Folkes | |
| 2004/0139230 A1 | 7/2004 | Kim | |
| 2004/0221047 A1 | 11/2004 | Grover | |
| 2004/0225627 A1 | 11/2004 | Botros | |
| 2004/0252683 A1 | 12/2004 | Kennedy | |
| 2005/0003832 A1 | 1/2005 | Osafune | |
| 2005/0028156 A1 | 2/2005 | Hammond | |
| 2005/0032581 A1* | 2/2005 | Wagner | A63B 24/0021 473/173 |
| 2005/0043060 A1 | 2/2005 | Brandenberg | |
| 2005/0050211 A1 | 3/2005 | Kaul | |
| 2005/0074001 A1 | 4/2005 | Mattes | |
| 2005/0149508 A1 | 7/2005 | Deshpande | |

(56) References Cited

U.S. PATENT DOCUMENTS

| | | |
|---|---|---|
| 2005/0159823 A1 | 7/2005 | Hayes |
| 2005/0198351 A1 | 9/2005 | Nog |
| 2005/0249196 A1 | 11/2005 | Ansari |
| 2005/0259637 A1 | 11/2005 | Chu |
| 2005/0262217 A1 | 11/2005 | Nonaka |
| 2005/0281288 A1 | 12/2005 | Banerjee |
| 2005/0289222 A1 | 12/2005 | Sahim |
| 2006/0010249 A1 | 1/2006 | Sabesan |
| 2006/0029102 A1 | 2/2006 | Abe |
| 2006/0039379 A1 | 2/2006 | Abe |
| 2006/0051055 A1 | 3/2006 | Ohkawa |
| 2006/0072523 A1 | 4/2006 | Richardson |
| 2006/0099973 A1 | 5/2006 | Nair |
| 2006/0129514 A1 | 6/2006 | Watanabe |
| 2006/0133343 A1 | 6/2006 | Huang |
| 2006/0173831 A1 | 8/2006 | Basso |
| 2006/0193295 A1 | 8/2006 | White |
| 2006/0206445 A1 | 9/2006 | Andreoli |
| 2006/0215684 A1 | 9/2006 | Capone |
| 2006/0223504 A1 | 10/2006 | Ishak |
| 2006/0256767 A1 | 11/2006 | Suzuki |
| 2006/0268792 A1 | 11/2006 | Belcea |
| 2007/0019619 A1 | 1/2007 | Foster |
| 2007/0073888 A1 | 3/2007 | Madhok |
| 2007/0094265 A1 | 4/2007 | Korkus |
| 2007/0112880 A1 | 5/2007 | Yang |
| 2007/0124412 A1 | 5/2007 | Narayanaswami |
| 2007/0127457 A1 | 6/2007 | Mirtorabi |
| 2007/0160062 A1 | 7/2007 | Morishita |
| 2007/0162394 A1 | 7/2007 | Zager |
| 2007/0171828 A1 | 7/2007 | Dalal |
| 2007/0189284 A1 | 8/2007 | Kecskemeti |
| 2007/0195765 A1 | 8/2007 | Heissenbuttel |
| 2007/0204011 A1 | 8/2007 | Shaver |
| 2007/0209067 A1 | 9/2007 | Fogel |
| 2007/0239892 A1 | 10/2007 | Ott |
| 2007/0240207 A1 | 10/2007 | Belakhdar |
| 2007/0245034 A1 | 10/2007 | Retana |
| 2007/0253418 A1 | 11/2007 | Shiri |
| 2007/0255677 A1 | 11/2007 | Alexander |
| 2007/0255699 A1 | 11/2007 | Sreenivas |
| 2007/0255781 A1 | 11/2007 | Li |
| 2007/0274504 A1 | 11/2007 | Maes |
| 2007/0276907 A1 | 11/2007 | Maes |
| 2007/0294187 A1 | 12/2007 | Scherrer |
| 2008/0005056 A1* | 1/2008 | Stelzig ............... H04L 65/1073 |
| 2008/0010366 A1 | 1/2008 | Duggan |
| 2008/0037420 A1 | 2/2008 | Tang |
| 2008/0043989 A1 | 2/2008 | Furutono |
| 2008/0046340 A1 | 2/2008 | Brown |
| 2008/0059631 A1 | 3/2008 | Bergstrom |
| 2008/0080440 A1 | 4/2008 | Yarvis |
| 2008/0101357 A1 | 5/2008 | Iovanna |
| 2008/0107034 A1 | 5/2008 | Jetcheva |
| 2008/0123862 A1 | 5/2008 | Rowley |
| 2008/0133583 A1 | 6/2008 | Artan |
| 2008/0133755 A1 | 6/2008 | Pollack |
| 2008/0151755 A1 | 6/2008 | Nishioka |
| 2008/0159271 A1 | 7/2008 | Kutt |
| 2008/0165775 A1 | 7/2008 | Das |
| 2008/0186901 A1 | 8/2008 | Itagaki |
| 2008/0200153 A1 | 8/2008 | Fitzpatrick |
| 2008/0215669 A1 | 9/2008 | Gaddy |
| 2008/0216086 A1 | 9/2008 | Tanaka |
| 2008/0243992 A1 | 10/2008 | Jardetzky |
| 2008/0250006 A1 | 10/2008 | Dettinger |
| 2008/0256359 A1 | 10/2008 | Kahn |
| 2008/0270618 A1 | 10/2008 | Rosenberg |
| 2008/0271143 A1 | 10/2008 | Stephens |
| 2008/0287142 A1 | 11/2008 | Keighran |
| 2008/0288580 A1 | 11/2008 | Wang |
| 2008/0298376 A1 | 12/2008 | Takeda |
| 2008/0320148 A1 | 12/2008 | Capuozzo |
| 2009/0006659 A1 | 1/2009 | Collins |
| 2009/0013324 A1 | 1/2009 | Gobara |
| 2009/0022154 A1 | 1/2009 | Kiribe |
| 2009/0024641 A1 | 1/2009 | Quigley |
| 2009/0030978 A1 | 1/2009 | Johnson |
| 2009/0037763 A1 | 2/2009 | Adhya |
| 2009/0052660 A1 | 2/2009 | Chen |
| 2009/0067429 A1 | 3/2009 | Nagai |
| 2009/0077184 A1 | 3/2009 | Brewer |
| 2009/0092043 A1 | 4/2009 | Lapuh |
| 2009/0097631 A1 | 4/2009 | Gisby |
| 2009/0103515 A1 | 4/2009 | Pointer |
| 2009/0113068 A1 | 4/2009 | Fujihira |
| 2009/0116393 A1 | 5/2009 | Hughes |
| 2009/0144300 A1 | 6/2009 | Chatley |
| 2009/0157887 A1 | 6/2009 | Froment |
| 2009/0185745 A1 | 7/2009 | Momosaki |
| 2009/0193101 A1 | 7/2009 | Munetsugu |
| 2009/0222344 A1 | 9/2009 | Greene |
| 2009/0228593 A1 | 9/2009 | Takeda |
| 2009/0254572 A1 | 10/2009 | Redlich |
| 2009/0268905 A1 | 10/2009 | Matsushima |
| 2009/0285209 A1 | 11/2009 | Stewart |
| 2009/0287835 A1 | 11/2009 | Jacobson |
| 2009/0288143 A1 | 11/2009 | Stebila |
| 2009/0288163 A1 | 11/2009 | Jacobson |
| 2009/0292743 A1 | 11/2009 | Bigus |
| 2009/0293121 A1 | 11/2009 | Bigus |
| 2009/0300079 A1 | 12/2009 | Shitomi |
| 2009/0300407 A1 | 12/2009 | Kamath |
| 2009/0307333 A1 | 12/2009 | Welingkar |
| 2009/0323632 A1 | 12/2009 | Nix |
| 2010/0005061 A1 | 1/2010 | Basco |
| 2010/0027539 A1 | 2/2010 | Beverly |
| 2010/0046546 A1 | 2/2010 | Ram |
| 2010/0057929 A1 | 3/2010 | Merat |
| 2010/0058346 A1 | 3/2010 | Narang |
| 2010/0088370 A1 | 4/2010 | Wu |
| 2010/0094767 A1 | 4/2010 | Miltonberger |
| 2010/0098093 A1 | 4/2010 | Ejzak |
| 2010/0100465 A1 | 4/2010 | Cooke |
| 2010/0103870 A1 | 4/2010 | Garcia-Luna-Aceves |
| 2010/0124191 A1 | 5/2010 | Vos |
| 2010/0125911 A1 | 5/2010 | Bhaskaran |
| 2010/0131660 A1 | 5/2010 | Dec |
| 2010/0150155 A1 | 6/2010 | Napierala |
| 2010/0165976 A1 | 7/2010 | Khan |
| 2010/0169478 A1 | 7/2010 | Saha |
| 2010/0169503 A1 | 7/2010 | Kollmansberger |
| 2010/0180332 A1 | 7/2010 | Ben-Yochanan |
| 2010/0182995 A1 | 7/2010 | Hwang |
| 2010/0185753 A1 | 7/2010 | Liu |
| 2010/0195653 A1 | 8/2010 | Jacobson |
| 2010/0195654 A1 | 8/2010 | Jacobson |
| 2010/0195655 A1 | 8/2010 | Jacobson |
| 2010/0217874 A1 | 8/2010 | Anantharaman |
| 2010/0232402 A1 | 9/2010 | Przybysz |
| 2010/0232439 A1 | 9/2010 | Dham |
| 2010/0235516 A1 | 9/2010 | Nakamura |
| 2010/0246549 A1 | 9/2010 | Zhang |
| 2010/0250497 A1 | 9/2010 | Redlich |
| 2010/0250939 A1 | 9/2010 | Adams |
| 2010/0268782 A1 | 10/2010 | Zombek |
| 2010/0272107 A1 | 10/2010 | Papp |
| 2010/0284309 A1 | 11/2010 | Allan |
| 2010/0284404 A1 | 11/2010 | Gopinath |
| 2010/0293293 A1 | 11/2010 | Beser |
| 2010/0322249 A1 | 12/2010 | Thathapudi |
| 2011/0013637 A1 | 1/2011 | Xue |
| 2011/0022812 A1 | 1/2011 | vanderLinden |
| 2011/0029952 A1 | 2/2011 | Harrington |
| 2011/0055392 A1 | 3/2011 | Shen |
| 2011/0055921 A1 | 3/2011 | Narayanaswamy |
| 2011/0060716 A1 | 3/2011 | Forman |
| 2011/0060717 A1 | 3/2011 | Forman |
| 2011/0090908 A1 | 4/2011 | Jacobson |
| 2011/0106755 A1 | 5/2011 | Hao |
| 2011/0145597 A1 | 6/2011 | Yamaguchi |
| 2011/0145858 A1 | 6/2011 | Philpott |
| 2011/0149858 A1 | 6/2011 | Hwang |
| 2011/0153840 A1 | 6/2011 | Narayana |

(56) References Cited

U.S. PATENT DOCUMENTS

| | | |
|---|---|---|
| 2011/0158122 A1 | 6/2011 | Murphy |
| 2011/0161408 A1 | 6/2011 | Kim |
| 2011/0202609 A1 | 8/2011 | Chaturvedi |
| 2011/0219427 A1 | 9/2011 | Hito |
| 2011/0231578 A1 | 9/2011 | Nagappan |
| 2011/0239256 A1 | 9/2011 | Gholmieh |
| 2011/0258049 A1 | 10/2011 | Ramer |
| 2011/0264824 A1 | 10/2011 | Venkata Subramanian |
| 2011/0265159 A1 | 10/2011 | Ronda |
| 2011/0265174 A1 | 10/2011 | Thornton |
| 2011/0271007 A1 | 11/2011 | Wang |
| 2011/0286457 A1 | 11/2011 | Ee |
| 2011/0286459 A1 | 11/2011 | Rembarz |
| 2011/0295783 A1 | 12/2011 | Zhao |
| 2011/0299454 A1 | 12/2011 | Krishnaswamy |
| 2012/0011170 A1 | 1/2012 | Elad |
| 2012/0011551 A1 | 1/2012 | Levy |
| 2012/0036180 A1 | 2/2012 | Thornton |
| 2012/0047361 A1 | 2/2012 | Erdmann |
| 2012/0066727 A1 | 3/2012 | Nozoe |
| 2012/0106339 A1 | 5/2012 | Mishra |
| 2012/0114313 A1 | 5/2012 | Phillips |
| 2012/0120803 A1 | 5/2012 | Farkas |
| 2012/0127994 A1 | 5/2012 | Ko |
| 2012/0136676 A1 | 5/2012 | Goodall |
| 2012/0136936 A1 | 5/2012 | Quintuna |
| 2012/0136945 A1 | 5/2012 | Lee |
| 2012/0137367 A1 | 5/2012 | Dupont |
| 2012/0141093 A1 | 6/2012 | Yamaguchi |
| 2012/0155464 A1 | 6/2012 | Kim |
| 2012/0158973 A1 | 6/2012 | Jacobson |
| 2012/0163373 A1 | 6/2012 | Lo |
| 2012/0179653 A1 | 7/2012 | Araki |
| 2012/0197690 A1 | 8/2012 | Agulnek |
| 2012/0198048 A1 | 8/2012 | Ioffe |
| 2012/0221150 A1 | 8/2012 | Arensmeier |
| 2012/0224487 A1 | 9/2012 | Hui |
| 2012/0257500 A1 | 10/2012 | Lynch |
| 2012/0284791 A1 | 11/2012 | Miller |
| 2012/0290669 A1 | 11/2012 | Parks |
| 2012/0290919 A1 | 11/2012 | Melnyk |
| 2012/0291102 A1 | 11/2012 | Cohen |
| 2012/0314580 A1 | 12/2012 | Hong |
| 2012/0317307 A1 | 12/2012 | Ravindran |
| 2012/0331112 A1 | 12/2012 | Chatani |
| 2013/0024560 A1 | 1/2013 | Vasseur |
| 2013/0041982 A1 | 2/2013 | Shi |
| 2013/0051392 A1 | 2/2013 | Filsfils |
| 2013/0060962 A1 | 3/2013 | Wang |
| 2013/0073552 A1 | 3/2013 | Rangwala |
| 2013/0074155 A1 | 3/2013 | Huh |
| 2013/0091539 A1 | 4/2013 | Khurana |
| 2013/0110987 A1 | 5/2013 | Kim |
| 2013/0111063 A1 | 5/2013 | Lee |
| 2013/0151584 A1 | 6/2013 | Westphal |
| 2013/0163426 A1 | 6/2013 | Beliveau |
| 2013/0166668 A1 | 6/2013 | Byun |
| 2013/0173822 A1 | 7/2013 | Hong |
| 2013/0182568 A1 | 7/2013 | Lee |
| 2013/0182931 A1 | 7/2013 | Fan |
| 2013/0185406 A1 | 7/2013 | Choi |
| 2013/0191412 A1 | 7/2013 | Kitamura |
| 2013/0197698 A1 | 8/2013 | Shah |
| 2013/0198119 A1 | 8/2013 | Eberhardt, III |
| 2013/0219038 A1 | 8/2013 | Lee |
| 2013/0219081 A1 | 8/2013 | Qian |
| 2013/0219478 A1 | 8/2013 | Mahamuni |
| 2013/0223237 A1 | 8/2013 | Hui |
| 2013/0227114 A1 | 8/2013 | Vasseur |
| 2013/0227166 A1 | 8/2013 | Ravindran |
| 2013/0242996 A1 | 9/2013 | Varvello |
| 2013/0250809 A1 | 9/2013 | Hui |
| 2013/0282854 A1 | 10/2013 | Jang |
| 2013/0282860 A1 | 10/2013 | Zhang |
| 2013/0282920 A1 | 10/2013 | Zhang |
| 2013/0304937 A1 | 11/2013 | Lee |
| 2013/0329696 A1 | 12/2013 | Xu |
| 2013/0336323 A1 | 12/2013 | Srinivasan |
| 2013/0339481 A1 | 12/2013 | Hong |
| 2013/0343408 A1 | 12/2013 | Cook |
| 2014/0003232 A1 | 1/2014 | Guichard |
| 2014/0006354 A1 | 1/2014 | Parkison |
| 2014/0006565 A1 | 1/2014 | Muscariello |
| 2014/0029445 A1 | 1/2014 | Hui |
| 2014/0032714 A1 | 1/2014 | Liu |
| 2014/0040505 A1 | 2/2014 | Barton |
| 2014/0040628 A1 | 2/2014 | Fort |
| 2014/0074730 A1 | 3/2014 | Arensmeier |
| 2014/0075567 A1 | 3/2014 | Raleigh |
| 2014/0082135 A1 | 3/2014 | Jung |
| 2014/0089454 A1 | 3/2014 | Jeon |
| 2014/0096249 A1 | 4/2014 | Dupont |
| 2014/0108474 A1 | 4/2014 | David |
| 2014/0115037 A1 | 4/2014 | Liu |
| 2014/0129736 A1 | 5/2014 | Yu |
| 2014/0136814 A1 | 5/2014 | Stark |
| 2014/0140348 A1 | 5/2014 | Perlman |
| 2014/0143370 A1 | 5/2014 | Vilenski |
| 2014/0146819 A1 | 5/2014 | Bae |
| 2014/0149733 A1 | 5/2014 | Kim |
| 2014/0156396 A1 | 6/2014 | deKozan |
| 2014/0165207 A1 | 6/2014 | Engel |
| 2014/0172783 A1 | 6/2014 | Suzuki |
| 2014/0172981 A1 | 6/2014 | Kim |
| 2014/0173034 A1 | 6/2014 | Liu |
| 2014/0173076 A1 | 6/2014 | Ravindran |
| 2014/0192717 A1 | 7/2014 | Liu |
| 2014/0195328 A1 | 7/2014 | Ferens |
| 2014/0195641 A1 | 7/2014 | Wang |
| 2014/0195666 A1 | 7/2014 | Dumitriu |
| 2014/0233575 A1 | 8/2014 | Xie |
| 2014/0237085 A1 | 8/2014 | Park |
| 2014/0245359 A1 | 8/2014 | DeFoy |
| 2014/0254595 A1 | 9/2014 | Luo |
| 2014/0280823 A1 | 9/2014 | Varvello |
| 2014/0281489 A1 | 9/2014 | Peterka |
| 2014/0281505 A1 | 9/2014 | Zhang |
| 2014/0282816 A1 | 9/2014 | Xie |
| 2014/0289325 A1 | 9/2014 | Solis |
| 2014/0289790 A1 | 9/2014 | Wilson |
| 2014/0314093 A1 | 10/2014 | You |
| 2014/0337276 A1 | 11/2014 | Iordanov |
| 2014/0365550 A1 | 12/2014 | Jang |
| 2015/0006896 A1 | 1/2015 | Franck |
| 2015/0018770 A1 | 1/2015 | Baran |
| 2015/0032892 A1 | 1/2015 | Narayanan |
| 2015/0039890 A1 | 2/2015 | Khosravi |
| 2015/0063802 A1 | 3/2015 | Bahadur |
| 2015/0089081 A1 | 3/2015 | Thubert |
| 2015/0095481 A1 | 4/2015 | Ohnishi |
| 2015/0095514 A1 | 4/2015 | Yu |
| 2015/0188770 A1 | 7/2015 | Naiksatam |
| 2015/0195149 A1 | 7/2015 | Vasseur |
| 2015/0207633 A1 | 7/2015 | Ravindran |
| 2017/0372268 A1* | 12/2017 | Ilan .................. G06Q 10/1095 |

FOREIGN PATENT DOCUMENTS

| | | |
|---|---|---|
| EP | 0295727 A2 | 12/1988 |
| EP | 0757065 A2 | 7/1996 |
| EP | 1077422 A2 | 2/2001 |
| EP | 1384729 A1 | 1/2004 |
| EP | 2124415 A2 | 11/2009 |
| EP | 2214357 A1 | 8/2010 |
| WO | 03005288 A2 | 1/2003 |
| WO | 03042254 A1 | 5/2003 |
| WO | 03049369 A2 | 6/2003 |
| WO | 03091297 A1 | 11/2003 |
| WO | 2007113180 A1 | 10/2007 |
| WO | 2007144388 A1 | 12/2007 |

(56) References Cited

FOREIGN PATENT DOCUMENTS

| | | |
|---|---|---|
| WO | 2011049890 A1 | 4/2011 |
| WO | 2013123410 | 8/2013 |

OTHER PUBLICATIONS

Koponen, Teemu et al., "A Data-Oriented (and Beyond) Network Architecture", SIGCOMM '07, Aug. 27-31, 2007, Kyoto, Japan, XP-002579021, p. 181-192.
Ao-Jan Su, David R. Choffnes, Aleksandar Kuzmanovic, and Fabian E. Bustamante. Drafting Behind Akamai: Inferring Network Conditions Based on CDN Redirections. IEEE/ACM Transactions on Networking {Feb. 2009).
"PBC Library-Pairing-Based Cryptography-About," http://crypto.stanford.edu/pbc. downloaded Apr. 27, 2015.
C. Gentry and A. Silverberg. Hierarchical ID-Based Cryptography. Advances in Cryptolog—ASIACRYPT 2002. Springer Berlin Heidelberg (2002).
Boneh et al., "Collusion Resistant Broadcast Encryption With Short Ciphertexts and Private Keys", 2005.
D. Boneh and M. Franklin. Identity-Based Encryption from the Weil Pairing. Advances in Cryptology—CRYPTO 2001, vol. 2139, Springer Berlin Heidelberg (2001).
Anteniese et al., "Improved Proxy Re-Encryption Schemes with Applications to Secure Distributed Storage", 2006.
Xiong et al., "CloudSeal: End-to-End Content Protection in Cloud-based Storage and Delivery Services", 2012.
J. Bethencourt, A, Sahai, and B. Waters, 'Ciphertext-policy attribute-based encryption,' in Proc. IEEE Security & Privacy 2007, Berkeley, CA, USA, May 2007, pp. 321-334.
J. Lotspiech, S. Nusser, and F. Pestoni. Anonymous Trust: Digit.
J. Shao and Z. Cao. CCA-Secure Proxy Re-Encryption without Pairings. Public Key Cryptography. Springer Lecture Notes in Computer Sciencevol. 5443 (2009).
Gopal et al. "Integrating content-based Mechanisms with hierarchical File systems", Feb. 1999, University of Arizona, 15 pages.
R. H. Deng, J. Weng, S. Liu, and K. Chen. Chosen-Ciphertext Secure Proxy Re-Encryption without Pairings. CANS. Spring Lecture Notes in Computer Science vol. 5339 (2008).
RTMP (2009). Available online at http://wwwimages.adobe.com/www.adobe.com/content/dam/Adobe/en/devnet/rtmp/ pdf/rtmp specification 1.0.pdf.
S. Chow, J. Weng, Y. Yang, and R. Deng. Efficient Unidirectional Proxy Re-Encryption. Progress in Cryptology—AFRICACRYPT 2010. Springer Berlin Heidelberg (2010).
S. Kamara and K. Lauter. Cryptographic Cloud Storage. Financial Cryptography and Data Security. Springer Berlin Heidelberg (2010).
Sandvine, Global Internet Phenomena Report—Spring 2012. Located online at http://www.sandvine.com/downloads/ documents/Phenomenal H 2012/Sandvine Global Internet Phenomena Report 1H 2012.pdf.
The Despotify Project (2012). Available online at http://despotify.sourceforge.net/.
V. K. Adhikari, S. Jain, Y. Chen, and Z.-L. Zhang. Vivisecting Youtube:An Active Measurement Study. In INFOCOM12 Miniconference (2012).
Vijay Kumar Adhikari, Yang Guo, Fang Hao, Matteo Varvello, Volker Hilt, Moritz Steiner, and Zhi-Li Zhang. Unreeling Netflix: Understanding and Improving Multi-CDN Movie Delivery. In the Proceedings of IEEE INFOCOM 2012 (2012).
Jacobson, Van et al. 'VoCCN: Voice Over Content-Centric Networks.' Dec. 1, 2009. ACM ReArch'09.
Rosenberg, J. "Interactive Connectivity Establishment (ICE): A Protocol for Network Address Translator (NAT) Traversal for Offer/Answer Protocols", Apr. 2010, pp. 1-117.
Shih, Eugene et al., 'Wake on Wireless: An Event Driven Energy Saving Strategy for Battery Operated Devices', Sep. 23, 2002, pp. 160-171.
Fall, K. et al., "DTN: an architectural retrospective", Selected areas in communications, IEEE Journal on, vol. 28, No. 5, Jun. 1, 2008, pp. 828-835.
Gritter, M. et al., 'An Architecture for content routing support in the Internet', Proceedings of 3rd Usenix Symposium on Internet Technologies and Systems, 2001, pp. 37-48.
"CCNx," http://ccnx.org/. downloaded Mar. 11, 2015.
"Content Delivery Network", Wikipedia, Dec. 10, 2011, http://en.wikipedia.org/w/index.php?title=Content_delivery_network &oldid=465077460.
"Digital Signature" archived on Aug. 31, 2009 at http://web.archive.org/web/20090831170721/http://en.wikipedia.org/wiki/Digital_signature.
"Introducing JSON," http://www.json.org/. downloaded Mar. 11, 2015.
"Microsoft PlayReady," http://www.microsoft.com/playready/. downloaded Mar. 11, 2015.
"Pursuing a pub/sub internet (PURSUIT)," http://www.fp7-pursuit.ew/PursuitWeb/. downloaded Mar. 11, 2015.
"The FP7 4WARD project," http://www.4ward-project.eu/. downloaded Mar. 11, 2015.
A. Broder and A. Karlin, "Multilevel Adaptive Hashing", Jan. 1990, pp. 43-53.
Detti, Andrea, et al. "CONET: a content centric inter-networking architecture." Proceedings of the ACM SIGCOMM workshop on Information-centric networking. ACM, 2011.
A. Wolman, M. Voelker, N. Sharma N. Cardwell, A. Karlin, and H.M. Levy, "On the scale and performance of cooperative web proxy caching," ACM SIGHOPS Operating Systems Review, vol. 33, No. 5, pp. 16-31, Dec. 1999.
Afanasyev, Alexander, et al. "Interest flooding attack and countermeasures in Named Data Networking." IFIP Networking Conference, 2013. IEEE, 2013.
B. Ahlgren et al., 'A Survey of Information-centric Networking' IEEE Commun. Magazine, Jul. 2012, pp. 26-36.
Bari, MdFaizul, et al. 'A survey of naming and routing in information-centric networks.' Communications Magazine, IEEE 50.12 (2012): 44-53.
Baugher, Mark et al., "Self-Verifying Names for Read-Only Named Data", 2012 IEEE Conference on Computer Communications Workshops (INFOCOM WKSHPS), Mar. 2012, pp. 274-279.
Brambley, Michael, A novel, low-cost, reduced-sensor approach for providing smart remote monitoring and diagnostics for packaged air conditioners and heat pumps. Pacific Northwest National Laboratory, 2009.
C.A. Wood and E. Uzun, "Flexible end-to-end content security in CCN," in Proc. IEEE CCNC 2014, Las Vegas, CA, USA, Jan. 2014.
Carzaniga, Antonio, Matthew J. Rutherford, and Alexander L. Wolf. 'A routing scheme for content-based networking.' INFOCOM 2004. Twenty-third Annual Joint Conference of the IEEE Computer and Communications Societies. vol. 2. IEEE, 2004.
Cho, Jin-Hee, Ananthram Swami, and Ray Chen. "A survey on trust management for mobile ad hoc networks." Communications Surveys & Tutorials, IEEE 13.4 (2011): 562-583.
Compagno, Alberto, et al. "Poseidon: Mitigating interest flooding DDoS attacks in named data networking." Local Computer Networks (LCN), 2013 IEEE 38th Conference on. IEEE, 2013.
Conner, William, et al. "A trust management framework for service-oriented environments." Proceedings of the 18th international conference on World wide web. ACM, 2009.
Content Centric Networking Project (CCN) [online], http://ccnx.org/releases/latest/doc/technical/, Downloaded Mar. 9, 2015.
Content Mediator Architecture for Content-aware Networks (COMET) Project [online], http://www.comet-project.org/, Downloaded Mar. 9, 2015.
D.K. Smetters, P. Golle, and J.D. Thornton, "CCNx access control specifications," PARC, Tech. Rep., Jul. 2010.
Dabirmoghaddam, Ali, Maziar Mirzazad Barijough, and J. J. Garcia-Luna-Aceves. 'Understanding optimal caching and opportunistic caching at the edge of information-centric networks.' Proceedings of the 1st international conference on Information-centric networking. ACM, 2014.

(56) References Cited

OTHER PUBLICATIONS

Detti et al., "Supporting the Web with an information centric network that routes by name", Aug. 2012, Computer Networks 56, pp. 3705-3702.

Dijkstra, Edsger W., and Carel S. Scholten. 'Termination detection for diffusing computations.' Information Processing Letters 11.1 (1980): 1-4.

Dijkstra, Edsger W., Wim HJ Feijen, and A_J M. Van Gasteren. "Derivation of a termination detection algorithm for distributed computations." Control Flow and Data Flow: concepts of distributed programming. Springer Berlin Heidelberg, 1986. 507-512.

E. Rescorla and N. Modadugu, "Datagram transport layer security," IETF RFC 4347, Apr. 2006.

E.W. Dijkstra, W. Feijen, and A.J.M. Van Gasteren, "Derivation of a Termination Detection Algorithm for Distributed Computations," Information Processing Letter, vol. 16, No. 5, 1983.

Fayazbakhsh, S. K., Lin, Y., Tootoonchian, A., Ghodsi, A., Koponen, T., Maggs, B., & Shenker, S. {Aug. 2013). Less pain, most of the gain: Incrementally deployable ICN. In ACM SIGCOMM Computer Communication Review (vol. 43, No. 4, pp. 147-158). ACM.

G. Tyson, S. Kaune, S. Miles, Y. El-Khatib, A. Mauthe, and A. Taweel, "A trace-driven analysis of caching in content-centric networks," In Proc. IEEE ICCCN 2012, Munich, Germany, Jul.-Aug. 2012, pp. 1-7.

G. Wang, Q. Liu, and J. Wu, "Hierarchical attribute-based encryption for fine-grained access control in cloud storage services," in Proc. ACM CCS 2010, Chicago, IL, USA, Oct. 2010, pp. 735-737.

G. Xylomenos et al., "A Survey of Information-centric Networking Research," IEEE Communication Surveys and Tutorials, Jul. 2013.

Garcia, Humberto E., Wen-Chiao Lin, and Semyon M. Meerkov. "A resilient condition assessment monitoring system." Resilient Control Systems (ISRCS), 2012 5th International Symposium on. IEEE, 2012.

Garcia-Luna-Aceves, Jose J. 'A unified approach to loop-free routing using distance vectors or link states.' ACM SIGCOMM Computer Communication Review. vol. 19. No. 4. ACM, 1989.

Garcia-Luna-Aceves, Jose J. 'Name-Based Content Routing in Information Centric Networks Using Distance Information' Proc ACM ICN 2014, Sep. 2014.

Ghali, Cesar, GeneTsudik, and Ersin Uzun. "Needle in a Haystack: Mitigating Content Poisoning in Named-Data Networking." Proceedings of NDSS Workshop on Security of Emerging Networking Technologies (SENT). 2014.

Ghodsi, Ali, et al. "Information-centric networking: seeing the forest for the trees." Proceedings of the 10th ACM Workshop on Hot Topics in Networks. ACM, 2011.

Ghodsi, Ali, et al. "Naming in content-oriented architectures." Proceedings of the ACM SIGCOMM workshop on Information-centric networking. ACM, 2011.

Gupta, Anjali, Barbara Liskov, and Rodrigo Rodrigues. "Efficient Routing for Peer-to-Peer Overlays." NSDI. vol. 4. 2004.

Heckerman, David, John S. Breese, and Koos Rommelse. "Decision-Theoretic Troubleshooting." Communications of the ACM. 1995.

Heinemeier, Kristin, et al. "Uncertainties in Achieving Energy Savings from HVAC Maintenance Measures in the Field." ASHRAE Transactions 118.Part 2 {2012).

Herlich, Matthias et al., "Optimizing Energy Efficiency for Bulk Transfer Networks", Apr. 13, 2010, pp. 1-3, retrieved for the Internet: URL:http://www.cs.uni-paderborn.de/fileadmin/informationik/ag-karl/publications/miscellaneous/optimizing.pdf (retrieved on Mar. 9, 2012).

Hoque et al., 'NLSR: Named-data Link State Routing Protocol', Aug. 12, 2013, ICN 2013, pp. 15-20.

https://code.google.com/p/ccnx-trace/.

I. Psaras, R.G. Clegg, R. Landa, W.K. Chai, and G. Pavlou, "Modelling and evaluation of CCN-caching trees," in Proc. IFIP Networking 2011, Valencia, Spain, May 2011, pp. 78-91.

Intanagonwiwat, Chalermek, Ramesh Govindan, and Deborah Estrin. 'Directed diffusion: a scalable and robust communication paradigm for sensor networks.' Proceedings of the 6th annual international conference on Mobile computing and networking. ACM, 2000.

J. Aumasson and D. Bernstein, "SipHash: a fast short-input PRf", Sep. 18, 2012.

J. Hur, "Improving security and efficiency in attribute-based data sharing," IEEE Trans. Knowledge Data Eng., vol. 25, No. 10, pp. 2271-2282, Oct. 2013.

V. Jacobson et al., 'Networking Named Content,' Proc. IEEE CoNEXT '09, Dec. 2009.

Jacobson et al., "Custodian-Based Information Sharing," Jul. 2012, IEEE Communications Magazine: vol. 50 Issue 7 (p. 3843).

Ji, Kun, et al. "Prognostics enabled resilient control for model-based building automation systems." Proceedings of the 12th Conference of International Building Performance Simulation Association. 2011.

K. Liang, L. Fang, W. Susilo, and D.S. Wong, "A Ciphertext-policy attribute-based proxy re-encryption with chosen-ciphertext security," in Proc. INCoS 2013, Xian, China, Sep. 2013, pp. 552-559.

Katipamula, Srinivas, and Michael R. Brambley. "Review article: methods for fault detection, diagnostics, and prognostics for building systemsa review, Part I." HVAC&R Research 11.1 (2005): 3-25.

Katipamula, Srinivas, and Michael R. Brambley. "Review article: methods for fault detection, diagnostics, and prognostics for building systemsa review, Part II." HVAC&R Research 11.2 (2005): 169-187.

L. Wang et al., 'OSPFN: an OSPF Based Routing Protocol for Named Data Networking,' Technical Report NDN-0003, 2012.

L. Zhou, V. Varadharajan, and M. Hitchens, "Achieving secure role-based access control on encrypted data in cloud storage," IEEE Trans. Inf. Forensics Security, vol. 8, No. 12, pp. 1947-1960, Dec. 2013.

Li, Wenjia, Anupam Joshi, and Tim Finin. "Coping with node misbehaviors in ad hoc networks: A multi-dimensional trust management approach." Mobile Data Management (MDM), 2010 Eleventh International Conference on. IEEE, 2010.

Lopez, Javier, et al. "Trust management systems for wireless sensor networks: Best practices." Computer Communications 33.9 (2010): 1086-1093.

M. Green and G. Ateniese, "Identity-based proxy re-encryption," in Proc. ACNS 2007, Zhuhai, China, Jun. 2007, pp. 288-306.

M. Ion, J. Zhang, and E.M. Schooler, "Toward content-centric privacy in ICN: Attribute-based encryption and routing," in Proc. ACM SIGCOMM ICN 2013, Hong Kong, China, Aug. 2013, pp. 39-40.

M. Naor and B. Pinkas "Efficient trace and revoke schemes," in Proc. FC 2000, Anguilla, British West Indies, Feb. 2000, pp. 1-20.

M. Nystrom, S. Parkinson, A. Rusch, and M. Scott, "PKCS#12: Personal information exchange syntax v. 1.1," IETF RFC 7292, K. Moriarty, Ed., Jul. 2014.

M. Parsa and J.J. Garcia-Luna-Aceves, "A Protocol for Scalable Loop-free Multicast Routing." IEEE JSAC, Apr. 1997.

M. Walfish, H. Balakrishnan, and S. Shenker, "Untangling the web from DNS," in Proc. USENIX NSDI 2004, Oct. 2010, pp. 735-737.

Mahadevan, Priya, et al. "Orbis: rescaling degree correlations to generate annotated internet topologies." ACM SIGCOMM Computer Communication Review. vol. 37. No. 4. ACM, 2007.

Mahadevan, Priya, et al. "Systematic topology analysis and generation using degree correlations." ACM SIGCOMM Computer Communication Review. vol. 36. No. 4. ACM, 2006.

Matocha, Jeff, and Tracy Camp. 'A taxonomy of distributed termination detection algorithms.' Journal of Systems and Software 43.3 (1998): 207-221.

Matteo Varvello et al., "Caesar: A Content Router for High Speed Forwarding", ICN 2012, Second Edition on Information-Centric Networking, New York, Aug. 2012.

McWilliams, Jennifer A., and Iain S. Walker. "Home Energy Article: A Systems Approach to Retrofitting Residential HVAC Systems." Lawrence Berkeley National Laboratory (2005).

(56) References Cited

OTHER PUBLICATIONS

Merindol et al., "An efficient algorithm to enable path diversity in link state routing networks", Jan. 10, Computer Networks 55 (2011), pp. 1132-1140.
Mobility First Project [online], http://mobilityfirst.winlab.rutgers.edu/, Downloaded Mar. 9, 2015.
Narasimhan, Sriram, and Lee Brownston. "HyDE-A General Framework for Stochastic and Hybrid Modelbased Diagnosis." Proc. DX 7 (2007): 162-169.
NDN Project [online], http://www.named-data.net/, Downloaded Mar. 9, 2015.
Omar, Mawloud, Yacine Challal, and Abdelmadjid Bouabdallah. "Certification-based trust models in mobile ad hoc networks: A survey and taxonomy." Journal of Network and Computer Applications 35.1 (2012): 268-286.
P. Mahadevan, E.Uzun, S. Sevilla, and J. Garcia-Luna-Aceves, "CCN-krs: A key resolution service for ccn," in Proceedings of the 1st International Conference on Information-centric Networking, Ser. INC 14 New York, NY, USA: ACM, 2014, pp. 97-106. [Online]. Available: http://doi.acm.org/10.1145/2660129.2660154.
S. Deering, "Multicast Routing in Internetworks and Extended LANs," Proc. ACM SIGCOMM '88, Aug. 1988.
S. Deering et al., "The PIM architecture for wide-area multicast routing," IEEE/ACM Trans, on Networking, vol. 4, No. 2, Apr. 1996.
S. Jahid, P. Mittal, and N. Borisov, "EASiER: Encryption-based access control in social network with efficient revocation," in Proc. ACM ASIACCS 2011, Hong Kong, China, Mar. 2011, pp. 411-415.
S. Kamara and K. Lauter, "Cryptographic cloud storage," in Proc. FC 2010, Tenerife, Canary Islands, Spain, Jan. 2010, pp. 136-149.
S. Kumar et al. "Peacock Hashing: Deterministic and Updatable Hashing for High Performance Networking," 2008, pp. 556-564.
S. Misra, R. Tourani, and N.E. Majd, "Secure content delivery in information-centric networks: Design, implementation, and analyses," in Proc. ACM SIGCOMM ICN 2013, Hong Kong, China, Aug. 2013, pp. 73-78.
S. Yu, C. Wang, K. Ren, and W. Lou, "Achieving secure, scalable, and fine-grained data access control in cloud computing," in Proc. IEEE INFOCOM 2010, San Diego, CA, USA, Mar. 2010, pp. 1-9.
S.J. Lee, M. Gerla, and C. Chiang, "On-demand Multicast Routing Protocol in Multihop Wireless Mobile Networks," Mobile Networks and Applications, vol. 7, No. 6, 2002.
Scalable and Adaptive Internet Solutions (SAIL) Project [online], http://sail-project.eu/ Downloaded Mar. 9, 2015.
Schein, Jeffrey, and Steven T. Bushby. A Simulation Study of a Hierarchical, Rule-Based Method for System-Level Fault Detection and Diagnostics in HVAC Systems. US Department of Commerce,[Technology Administration], National Institute of Standards and Technology, 2005.
Shani, Guy, Joelle Pineau, and Robert Kaplow. "A survey of point-based POMDP solvers." Autonomous Agents and Multi-Agent Systems 27.1 (2013): 1-51.
Sheppard, John W., and Stephyn GW Butcher. "A formal analysis of fault diagnosis with d-matrices." Journal of Electronic Testing 23.4 (2007): 309-322.
Shneyderman, Alex et al., 'Mobile VPN: Delivering Advanced Services in Next Generation Wireless Systems', Jan. 1, 2003, pp. 3-29.
Solis, Ignacio, and J. J. Garcia-Luna-Aceves. 'Robust content dissemination in disrupted environments.' proceedings of the third ACM workshop on Challenged networks. ACM, 2008.
Sun, Ying, and Daniel S. Weld. "A framework for model-based repair." AAAI. 1993.
T. Ballardie, P. Francis, and J. Crowcroft, "Core Based Trees (CBT)," Proc. ACM SIGCOMM '88, Aug. 1988.
T. Dierts, "The transport layer security (TLS) protocol version 1.2," IETF RFC 5246, 2008.
T. Koponen, M. Chawla, B.-G. Chun, A. Ermolinskiy, K.H. Kim, S. Shenker, and I. Stoica, 'A data-oriented (and beyond) network architecture,' ACM SIGCOMM Computer Communication Review, vol. 37, No. 4, pp. 181-192, Oct. 2007.
V. Goyal, 0. Pandey, A. Sahai, and B. Waters, "Attribute-based encryption for fine-grained access control of encrypted data," in Proc. ACM CCS 2006, Alexandria, VA, USA, Oct.-Nov. 2006, pp. 89-98.
V. Jacobson, D.K. Smetters, J.D. Thornton, M.F. Plass, N.H. Briggs, and R.L. Braynard, 'Networking named content,' in Proc. ACM CoNEXT 2009, Rome, Italy, Dec. 2009, pp. 1-12.
Verma, Vandi, Joquin Fernandez, and Reid Simmons. "Probabilistic models for monitoring and fault diagnosis." The Second IARP and IEEE/RAS Joint Workshop on Technical Challenges for Dependable Robots in Human Environments. Ed. Raja Chatila. Oct. 2002.
Vutukury, Srinivas, and J. J. Garcia-Luna-Aceves. A simple approximation to minimum-delay routing. vol. 29. No. 4. ACM, 1999.
W.-G. Tzeng and Z.-J. Tzeng, "A public-key traitor tracing scheme with revocation using dynamic shares," in Proc. PKC 2001, Cheju Island, Korea, Feb. 2001, pp. 207-224.
Waldvogel, Marcel "Fast Longest Prefix Matching: Algorithms, Analysis, and Applications", A dissertation submitted to the Swiss Federal Institute of Technology Zurich, 2002.
Walker, Iain S. Best practices guide for residential HVAC Retrofits. No. LBNL-53592. Ernest Orlando Lawrence Berkeley National Laboratory, Berkeley, CA (US), 2003.
Wang, Jiangzhe et al.,"DMND: Collecting Data from Mobiles Using Named Data", Vehicular Networking Conference, 2010 IEEE, pp. 49-56. .
Xylomenos, George, et al. "A survey of information-centric networking research." Communications Surveys & Tutorials, IEEE 16.2 (2014): 1024-1049.
Yi, Cheng, et al. 'A case for stateful forwarding plane.' Computer Communications 36.7 (2013): 779-791.
Yi, Cheng, et al. 'Adaptive forwarding in named data networking.' ACM SIGCOMM computer communication review 42.3 (2012): 62-67.
Zahariadis, Theodore, et al. "Trust management in wireless sensor networks." European Transactions on Telecommunications 21.4 (2010): 386-395.
Zhang, et al., "Named Data Networking (NDN) Project", http://www.parc.com/publication/2709/named-data-networking-ndn-project.html, Oct. 2010, NDN-0001, PARC Tech Report.
Zhang, Lixia, et al. 'Named data networking.' ACM SIGCOMM Computer Communication Review 44.3 {2014): 66-73.
Soh et al., "Efficient Prefix Updates for IP Router Using Lexicographic Ordering and Updateable Address Set", Jan. 2008, IEEE Transactions on Computers, vol. 57, No. 1.
Beben et al., "Content Aware Network based on Virtual Infrastructure", 2012 13th ACIS International Conference on Software Engineering.
Biradar et al., "Review of multicast routing mechanisms in mobile ad hoc networks", Aug. 16, Journal of Network and Computer Applications 35 (2012) 221-229.
D. Trossen and G. Parisis, "Designing and realizing and information-centric internet," IEEE Communications Magazing, vol. 50, No. 7, pp. 60-67, Jul. 2012.
Garcia-Luna-Aceves et al., "Automatic Routing Using Multiple Prefix Labels", 2012, IEEE, Ad Hoc and Sensor Networking Symposium.
Gasti, Paolo et al., 'DoS & DDoS in Named Data Networking', 2013 22nd International Conference on Computer Communications and Networks (ICCCN), Aug. 2013, pp. 1-7.
Ishiyama, "On the Effectiveness of Diffusive Content Caching in Content-Centric Networking", Nov. 5, 2012, IEEE, Information and Telecommunication Technologies (APSITT), 2012 9th Asia-Pacific Symposium.
J. Hur and D.K. Noh, "Attribute-based access control with efficient revocation in data outsourcing systers," IEEE Trans. Parallel Distrib. Syst, vol. 22, No. 7, pp. 1214-1221, Jul. 2011.
Kaya et al., "A Low Power Lookup Technique for Multi-Hashing Network Applications", 2006 IEEE Computer Society Annual Symposium on Emerging VLSI Technologies and Architectures, Mar. 2006.

(56) References Cited

OTHER PUBLICATIONS

Hoque et al., "NLSR: Named-data Link State Routing Protocol", Aug. 12, 2013, ICN'13.

Nadeem Javaid, "Analysis and design of quality link metrics for routing protocols in Wireless Networks", PhD Thesis Defense, Dec. 15, 2010, Universete Paris-Est.

Wetherall, David, "Active Network vision and reality: Lessons form a capsule-based system", ACM Symposium on Operating Systems Principles, Dec. 1, 1999. pp. 64-79.

Kulkarni A.B. et al., "Implementation of a prototype active network", IEEE, Open Architectures and Network Programming, Apr. 3, 1998, pp. 130-142.

Xie et al. "Collaborative Forwarding and Caching in Content Centric Networks", Networking 2012.

Amadeo et al. "Design and Analysis of a Transport-Level Solution for Content-Centric VANETs", University "Mediterranea" of Reggio Calabria, Jun. 15, 2013.

Lui et al. (A TLV-Structured Data Naming Scheme for Content-Oriented Networking, pp. 5822-5827, International Workshop on the Network of the Future, Communications (ICC), 2012 IEEE International Conference on Jun. 10-15, 2012).

Peter Dely et al. "OpenFlow for Wireless Mesh Networks" Computer Communications and Networks, 2011 Proceedings of 20th International Conference on, IEEE, Jul. 31, 2011 (Jul. 31, 2011), pp. 1-6.

Garnepudi Parimala et al "Proactive, reactive and hybrid multicast routing protocols for Wireless Mesh Networks", 2013 IEEE International Conference on Computational Intelligence and Computing Research, IEEE, Dec. 26, 2013, pp. 1-7.

Tiancheng Zhuang et al. "Managing Ad Hoc Networks of Smartphones", International Journal of Information and Education Technology, Oct. 1, 2013.

\* cited by examiner

DEVICE HEALTH ESTIMATION BY COMBINING CONTEXTUAL INFORMATION WITH SENSOR DATA

FIELD

The present disclosure generally relates to estimating device health. More specifically, the present disclosure relates to a method and system for accurately diagnosing device failure by combining a device's operating context with sensor data.

RELATED ART

The growing Internet of Things is predicted to connect 30 billion devices by 2020. This will bring in tremendous amounts of data and drive the innovations needed to realize the vision of Industry 4.0, which includes cyber-physical systems monitoring physical processes, and communicating and cooperating with each other and with humans in real time. One of the key challenges is how to analyze large amounts of data to provide useful and actionable information for business intelligence and decision making. In particular, one challenge is to prevent unexpected downtime and its significant impact on overall equipment effectiveness (OEE) and total cost of ownership (TCO) in many industries. Continuous monitoring of equipment and early detection of incipient faults can support optimal maintenance strategies, prevent downtime, increase productivity, and reduce costs. To that end, there have been a number of anomaly detection and diagnosis methods proposed for detecting machine fault and estimating machine health.

Some have proposed applying different approaches to detect anomalies for various types of equipment, including statistical methods, neural network methods, and reliability methods. Some approaches focus on analyzing, combining, and modeling sensor data (e.g. vibration, current, acoustics signal) to detect machine faults. However, in some cases, these approaches may generate false alarms. Previous approaches have also used vibration data and/or acceleration data for diagnosing machine imbalance fault conditions. Other approaches may use temperature data to diagnose faults. However, it can be expensive to acquire vibration data and it may be difficult and insufficiently accurate to use temperature data to perform diagnostics.

SUMMARY

One embodiment of the present invention provides a method for detecting fault in a machine. During operation, the system obtains a plurality of control signals associated with controlling the machine and sensor data that indicates a condition of the machine during a time period when the plurality of control signals control the machine. The system then determines consistent time intervals for each of the plurality of control signals, in which during a consistent time interval the standard deviation of a respective control signal is less than a respective predetermined threshold. The system may aggregate the consistent time intervals of the plurality of control signals to determine aggregate consistent intervals. The system then maps the aggregate consistent intervals of the plurality of control signals to the sensor data to determine a plurality of time interval segments for the sensor data. The system may generate a plurality of features based on the sensor data, in which each respective feature is generated from a time interval segment of the plurality of time interval segments for the sensor data. The system may then train a classifier using the plurality of features, and subsequently apply the classifier to additional sensor data indicating a condition of the machine over a period of time to detect a machine fault.

In one variation on this embodiment, the plurality of control signals includes spindle motor speed, spindle load, and actual spindle speed, and the sensor data is temperature data indicating a temperature associated with the machine.

In one variation on this embodiment, aggregating the consistent time intervals includes determining an intersection of sets of consistent time intervals over all control signals.

In one variation on this embodiment, generating the features includes computing an average, a standard deviation, a maximum fast Fourier transform (FFT) value, and a FFT frequency at maximum amplitude for the sensor data.

In a further variation on this embodiment, the generated features form a high-dimensional feature space. The system also applies principal component analysis (PCA) to project the high-dimensional feature space into a low-dimensional space, and applies linear discriminant analysis (LDA) to determine an optimal coordinate transformation that provides maximum separation between classes.

In a further variation on this embodiment, determining consistent time intervals further includes generating a temporal segment representation of the machine's operation context.

In a further variation on this embodiment, applying the classifier further includes generating features for the classifier with same conditions as in classifier training by determining time intervals of a primary control signal that have same values for the primary control signal as a value of the primary control signal when generating training features.

In a further variation on this embodiment, the system removes one or more control signal intervals that are inconsistent from the plurality of control signals.

BRIEF DESCRIPTION OF THE FIGURES

In the figures, like reference numerals refer to the same figure elements.

DETAILED DESCRIPTION

Figure 1:
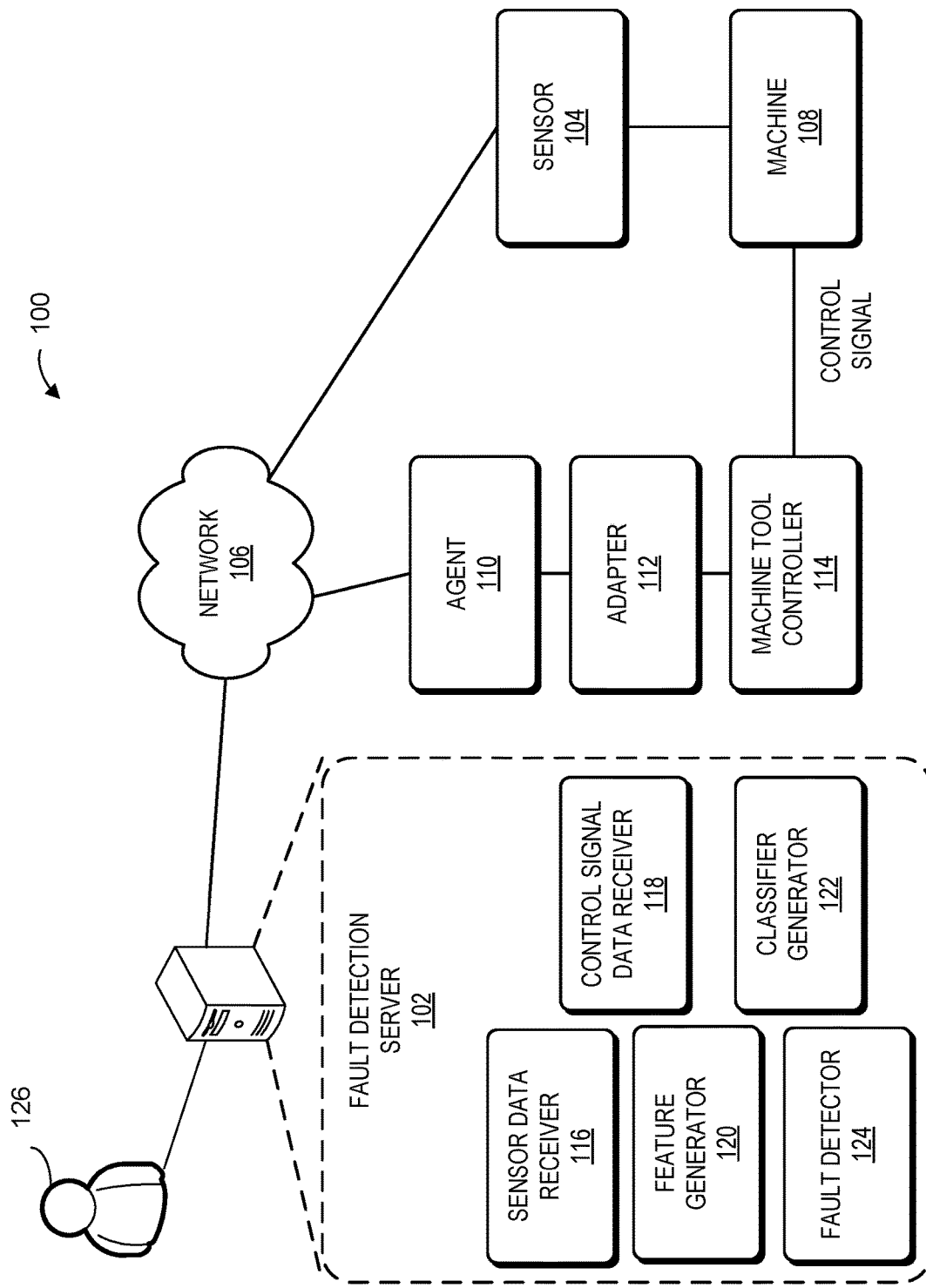
FIG. 1 presents a diagram illustrating an exemplary machine fault detection system, in accordance with an embodiment of the present invention.

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

Overview

Embodiments of the present invention solve the problem of diagnosing machine fault in the absence of vibration data by training a classifier to intelligently combine device operating context information and sensor data to detect abnormal conditions and accurately diagnose device failure. This disclosure describes a data fusion method that combines sensor data indicating the condition of a machine tool with the machine's operating context to detect machine faults. A fault detection system may train a classifier to detect machine faults using features generated from the sensor data. One or more sensors can monitor the machine tool and provide streams of sensor data indicating the condition of the machine tool, including sensor data such as temperature data. Contextual data may include data indicating multiple control signals used to control and operate the machine tool.

The system can leverage contextual information to classify sensor data more accurately. By accounting for environmental or external input (e.g., fluctuations in control signals) the system can reduce or eliminate the number of false alarms. For example, the system may diagnose imbalance of a machine tool that has a cutting tool attached to a spindle. The spindle rotates to turn the cutting tool. A machine tool controller may use closed-loop control with multiple control signals to control the machine. Some of these control signals include control signals for spindle motor speed, spindle load, and actual spindle speed. The control signals may fluctuate and that can affect the output or condition of the machine. The system can train the classifier using only temperature data that correspond to those portions of the control signals that are stable and avoid the fluctuating input signals. This improves the accuracy of the classifier when the system applies the classifier to temperature data that corresponds to stable segments of the control signals with the same control signal conditions.

The system determines the time intervals at which the control signals are consistent (or constant) and uses the consistent intervals to segmentize corresponding sensor data. For example, the control signals may be consistent during some interval with a standard deviation equal to or below a predetermined threshold (e.g., a standard deviation of zero). The system defines a temporal segment for each of the consistent portions of the control signals and may generate aggregated segments that each represents an aggregation of the temporal segments. The system then maps the aggregated segments to the temperature sensor data to define segments in the temperature sensor data. The system uses the segments in the temperature sensor data as features to train a classifier. For example, some of the features may include average, standard deviation, maximum fast Fourier transform (FFT) value, and FFT frequency at maximum amplitude for a segment. The system thus extracts features from the temperature sensor data using the contextual information derived from the control signals. The system trains a classifier using the extracted features. The system can use the trained classifier to detect machine faults for sensor data that corresponds to consistent control signal conditions. The classifier can detect (or predict) abnormal or anomalous temperature sensor data coming from the machine, and can alert a machine operator that there may be an current (or upcoming) problem with the machine.

Thus, by considering the machine's operating context, the system can analyze the device's health condition and diagnose device failure using cheaper sensor data, without needing to use vibration data that may be ideal but is more to expensive to acquire.

Exemplary Machine Fault Detection System

FIG. 1 presents a diagram illustrating an exemplary machine fault detection system 100, in accordance with an embodiment of the present invention. Machine fault detection system 100 includes a fault detection server 102 communicating with one or more sensors 104 over a network 106 that can detect the current condition of a machine 108 and provide continuous sensor data that indicates the condition of machine 108. For example, sensor 104 may provide continuous temperature data for machine 108 by measuring and/or detecting the temperature of the machine. Server 102 may also communicate with an agent 110. Agent 110 may communicate with an adapter 112 to retrieve control signal data.

System 100 may use MTConnect to diagnose machine health condition by combining sensor data with operating context information. MTConnect is an open-source communication protocol designed to allow machine tools and other equipment to talk to one another and to computer programs that process data from the machines. MTConnect was developed to connect various legacy machines independent of the controller providers. MTConnect allows for monitoring machine operating context in real-time.

In one embodiment, agent 110 may format control signal data received from adapter 112 into an MTConnect standard XML stream, and respond to HTTP requests by returning the appropriate control signal data. In some embodiments, agent 110 can also send control signal data to server 102 as agent 110 collects the data. Adapter 112 collects and filters data that includes control signal data from a machine tool controller 114, and sends the collected data to agent 110.

Machine tool controller 114 may control machine 108 with closed-loop control and multiple control signals. Examples of control signals include spindle motor speed, spindle load, actual spindle speed and Y drive load. Machine controller 114 may use feedback from the current state of the machine to control machine 108.

Fault detection server 102 may use the sensor data to detect problems with machine 108. Fault detection server 102 may include a sensor data receiver 116, a control signal data receiver 118, a feature generator 120, a classifier generator 122, and a fault detector 124.

Sensor data receiver 116 may receive continuously streaming (e.g., time series) sensor data from sensor 104. Control signal data receiver 118 may receive control signal data from agent 110. Feature generator 120 may analyze a control signal to determine consistent intervals and aggregate time intervals, and map the aggregate time intervals to time series sensor data (e.g., indicating temperature of machine 108) to segmentize the sensor data and generate features. Classifier generator 122 may generate a classifier by training the classifier on the generated features.

Fault detector 124 may apply the generated classifier to sensor data and control signal input (e.g., in the form of temporal segments) in order to detect machine faults. In some embodiments, fault detector 124 may utilize feature generator 120 to generate features from sensor data using control signal input so that the classifier can classify sensor data segments under the same control signal conditions that the classifier is trained with. Further, some implementations may utilize different sensors and/or additional sensors to detect or measure other machine conditions.

System 100 may diagnose any fault with machine 108. For example, system 100 may detect imbalance problems with machine 108. System 100 may determine a degree of imbalance for machine 108. Machine 108 may be a machine tool with a spindle holding a cutting tool. For example, there may be an imbalance problem if the machine tool, spindle, and/or cutting tool is incorrectly positioned.

System 100 can diagnose any fault using a combination of contextual data (e.g., control signal) received from agent 110 and sensor data that complement each other. System 100 can use the contextual data to discretize (e.g., segmentize) the sensor data and train a classifier using features generated from the sensor data segments. System 100 can apply the classifier to detect faults in machine 108, and alert an operator 126.

Generating a Classifier

Figure 2:
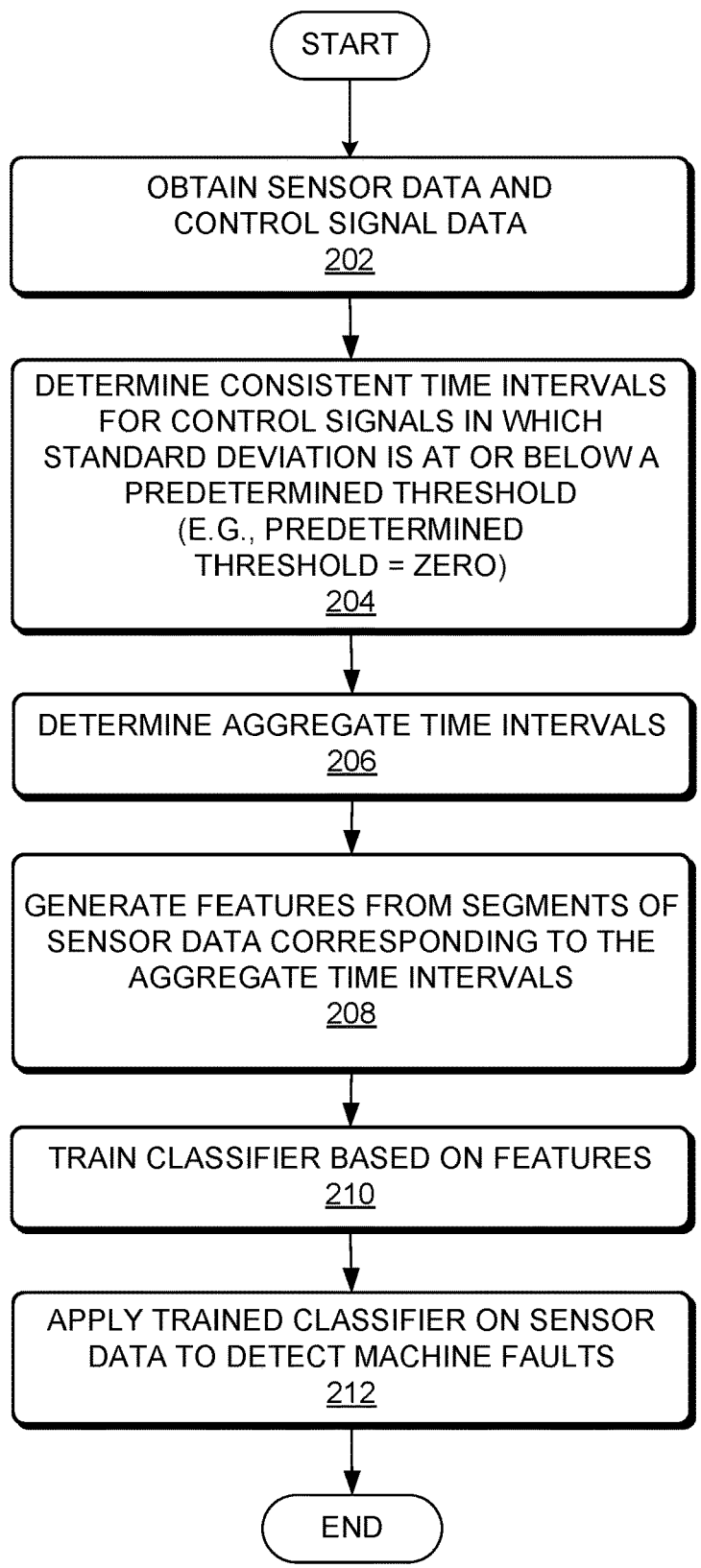
FIG. 2 presents a flow chart illustrating an exemplary process to generate a classifier for detecting machine faults, in accordance with an embodiment of the present invention.

FIG. 2 presents a flow chart illustrating an exemplary process to generate a classifier for detecting machine faults, in accordance with an embodiment of the present invention. Embodiments of the present invention are not limited to the operations depicted in FIG. 2, and some embodiments may perform the operations of FIG. 2 in a different order or with operations that vary from that depicted in FIG. 2

As depicted in FIG. 2, the system may initially obtain sensor data and control signal data (operation 202). For example, the system may obtain multiple control signals such as a control signal for controlling a spindle motor speed, a control signal for spindle load, and a control signal for actual spindle speed. The system may also obtain continuously streaming (e.g., time series) sensor data such as the temperature data for a machine. In some embodiments, the system can also obtain other time series sensor data from additional sensors or different sensor types not depicted in FIG. 1.

The system may then perform a segmentation technique that provides a temporal representation of the machine's operation context, and combine the temporal representation with sensor data to estimate machine health.

The system may analyze the control signal data to determine consistent time intervals for control signals (operation 204). These are time intervals that have a standard deviation at or below a minimum predetermined threshold (e.g., the predetermined threshold may be zero).

Figure 3:
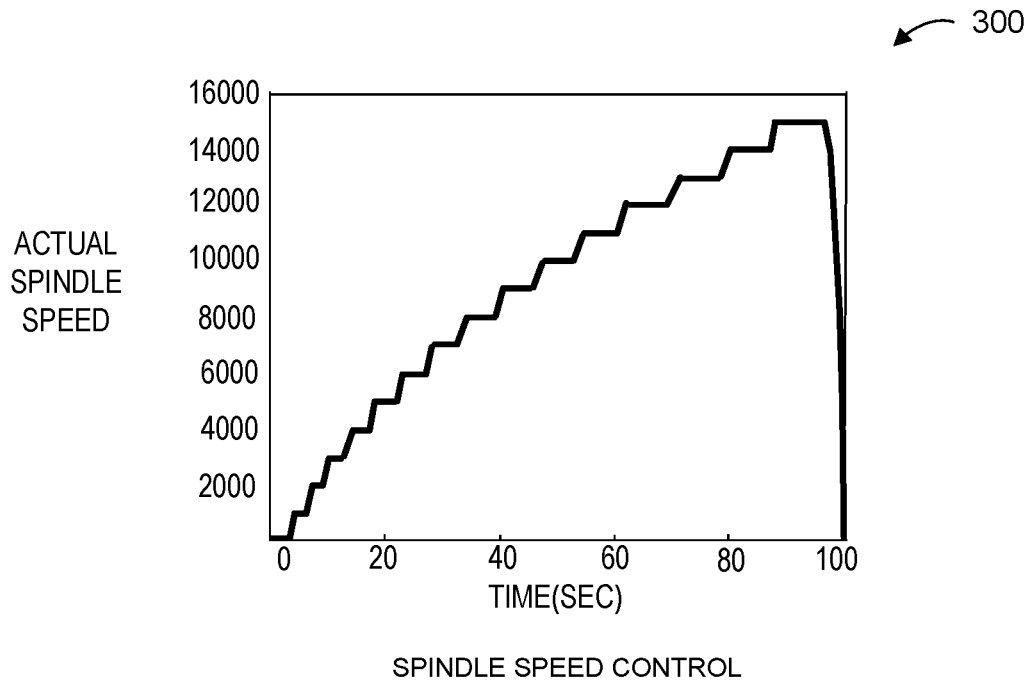
FIG. 3 illustrates an exemplary graph of the result of a temporal segmentation scheme with spindle speed control.

In some embodiments, to utilize the control signals to provide temporal segmentation, e.g., assuming quasi-steady state, the system determines the time intervals in which the following conditions are satisfied: (i) all experiments display same values (e.g., result in same values) for the primary control signal (e.g., actual spindle speed) and (ii) all the control signals are constant over the same period. Note that, to determine the dynamic response, rather than quasi steady state response, the control signals should be consistent across the experiments so that responses are compared under the same set of control inputs. FIG. 3 shows a graph 300 illustrating the result of this temporal segmentation scheme with the spindle speed control. In some embodiments, the classifier classifies sensor data corresponding to control signal input (e.g., consistent time intervals) that satisfies these conditions. For example, the value of the primary control signal is the same for features when applying a classifier and for features when training the classifier. As another example, all control signals are constant over the same time period for features when applying the classifier and for features when training the classifier.

Figure 4:
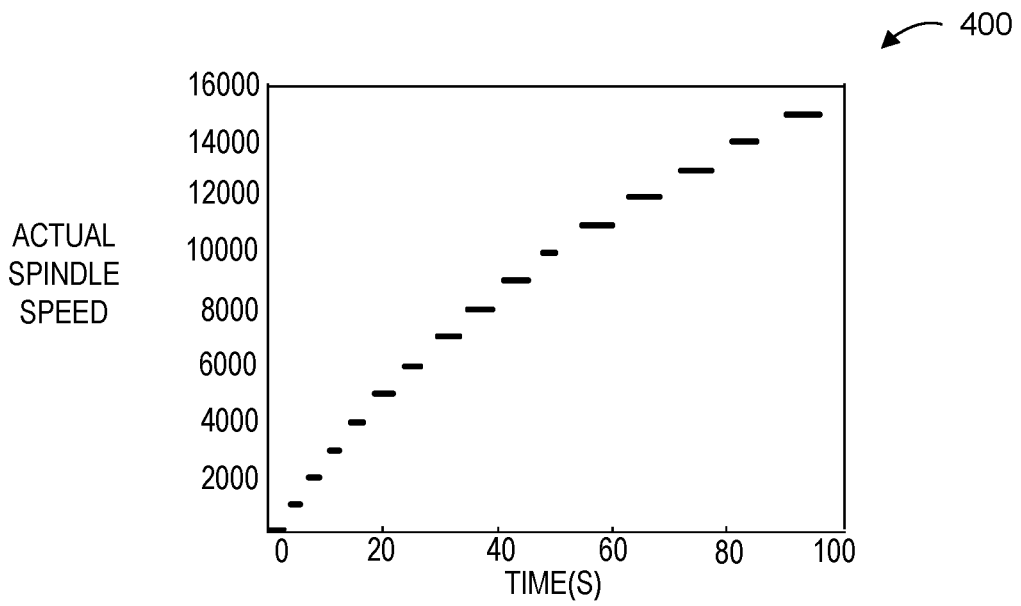
FIG. 4 illustrates an exemplary graph of spindle speed control with consistent time segments.

In some embodiments, there may be multiple control signals. For each sample time, the system may compute the standard deviation for each control signal separately (e.g., zero standard deviation shows a control signal which has the same value for all the sample data). In other words, for each of the control signals, the system may compute the standard deviation at each time step (e.g., time interval). The system may identify the periods with standard deviation at or below a predetermined threshold to find the consistent time intervals. For example, the predetermined threshold may be zero. For example, FIG. 4 illustrates a graph 400 showing consistent time intervals as 16 segments along the time axis. The system may remove one or more control signals that are inconsistent (e.g., this assumes that these control signals are secondary feedback signals). In some embodiments, the system may remove one or more inconsistent control signal intervals.

Figure 5:
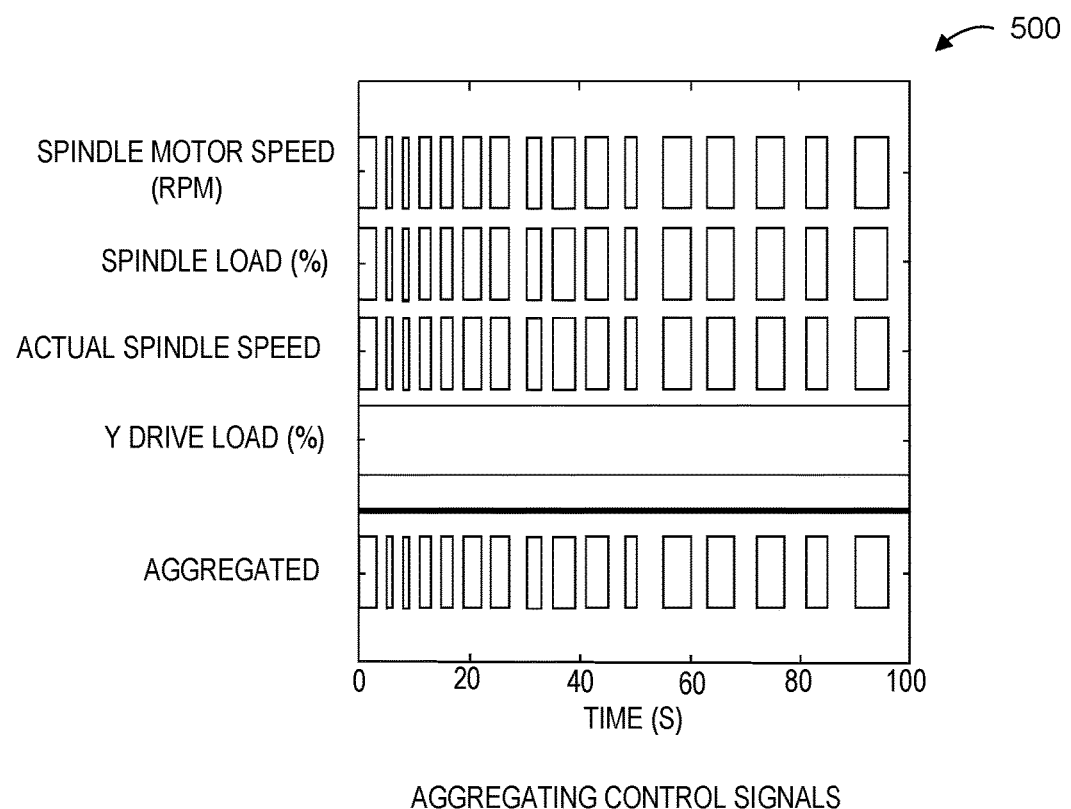
FIG. 5 illustrates an exemplary diagram of aggregating control signals.

The system can determine the intersection of the sets of consistent time intervals over all (or a plurality of) the control signals to determine the aggregate time intervals (e.g., temporal segments) over which the control signals are statistically consistent (operation 206). This is illustrated by a graph 500 in FIG. 5. For example, the system may determine that there are 16 temporal segments for the control signals, as depicted in the graphs 400, 500 in FIG. 4-FIG. 5.

System 100 may then generate features from segments of the sensor data that correspond to the aggregate time intervals for the control signals (operation 208). The system may map the aggregate time intervals (e.g., temporal segments) that are consistent to the sensor data to segmentize the sensor data. The system may analyze each segment of the time series for sensor data separately, and decompose the sensor data into features using time-domain and frequency domain analysis. For example, for each segment, system 100 may generate features such as the average, standard deviation, maximum FFT value, and FFT frequency at maximum amplitude. These features characterize or summarize observations of the sensor data for a segment. The generated features may form a high-dimensional feature space. For the examples depicted in FIG. 3-FIG. 7 the system may determine that there are 16 temporal segments, and the system may generate a 64 dimensional feature space to diagnose machine imbalance.

In some embodiments, the system projects the high-dimensional data to a much smaller sub-space to prevent over-fitting. The system may use linear transformation-based approaches. The system may use principal component analysis (PCA) to project a high-dimensional feature space into a low-dimensional space followed by a linear discriminant analysis (LDA) to search the optimal separation among various device health conditions. For example, the system may use PCA to reduce the dimensionality from 64 to 4. The system may use LDA to determine the optimal coordinate transformation that provides maximum separation between classes.

Figure 6:
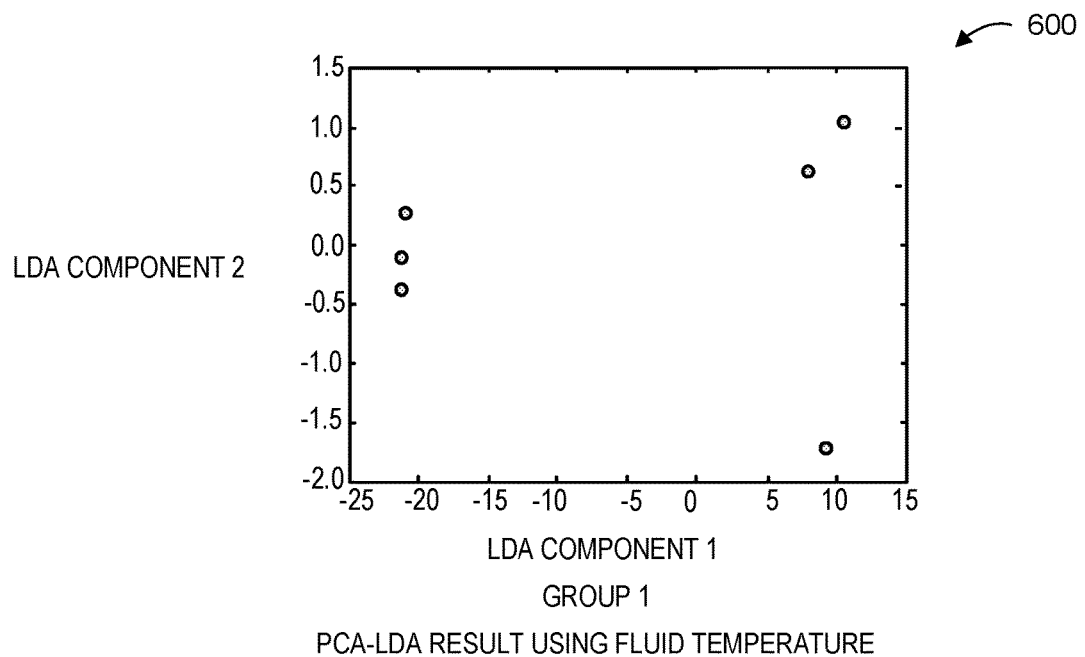
FIG. 6 illustrates an exemplary graph of principal component analysis-linear discriminant analysis results for group 1.
Figure 7:
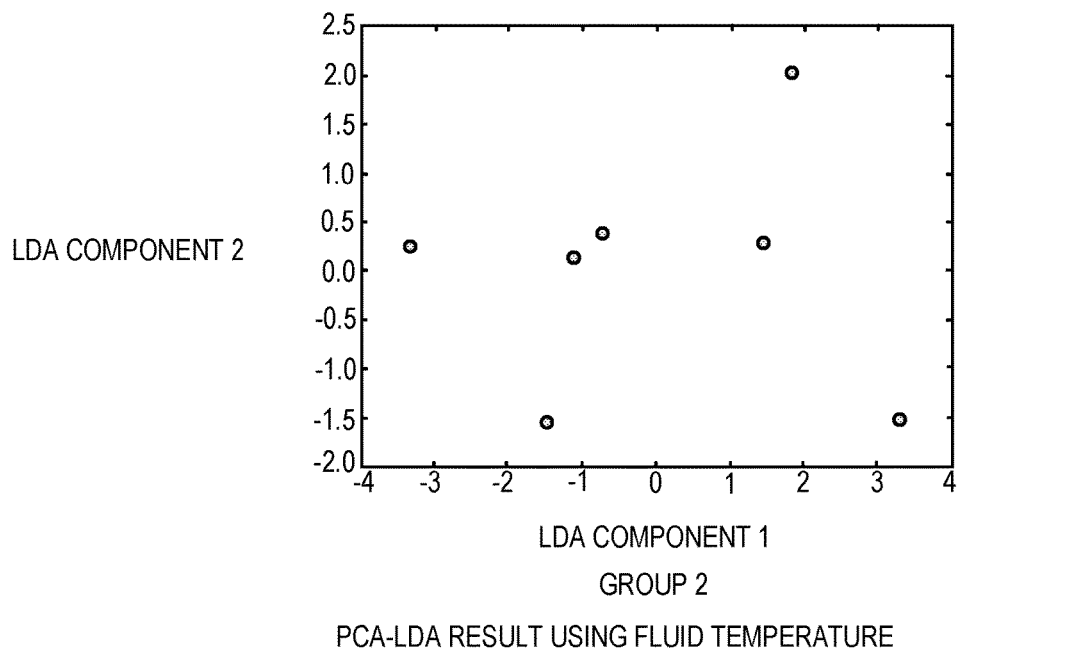
FIG. 7 illustrates an exemplary graph of principal component analysis-linear discriminant analysis results for group 2.

FIG. 6 and FIG. 7 illustrates graphs 600, 700 showing the results of PCA-LDA analysis for fluid temperature sensor data. The inventors determined from experimental results that a temperature sensor located at a motor also exhibited diagnostic capability after applying control-based temporal segmentation. Note that besides temperature sensor data, system 100 can use any other suitable streams of sensor data indicating the condition of the machine, such as pressure sensor data. System 100 can generate features from segments using different types or combinations of sensor data. In some embodiments, system 100 can also generate a classifier using other types of control signals and combinations of control signals besides the control signals described in this specification.

The system may then train a classifier based on the features (operation 210). System 100 may use any type of classifier, including examples such as decision tree classifiers, naive Bayes classifiers, support vector machines, rule-based classifiers, and neural networks. System 100 may apply the trained classifier on streaming temperature sensor data indicating the condition of the machine to predict upcoming machine faults or detect current machine faults (operation 212). In one embodiment, the classifier may classify sensor data that corresponds to control signals matching the same conditions as the control signals used in training the classifier.

Exemplary Apparatus

Figure 8:
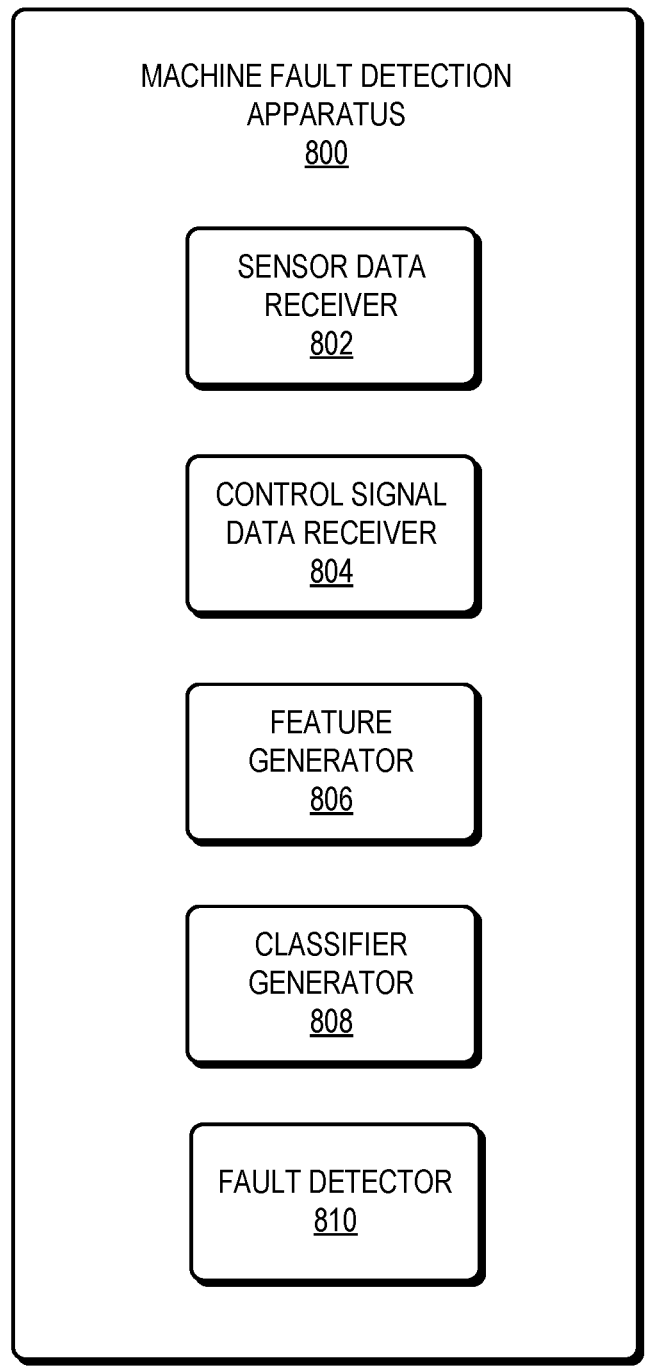
FIG. 8 illustrates an exemplary fault detection apparatus, in accordance with an embodiment.

FIG. 8 presents a block diagram illustrating an exemplary apparatus 800 for detecting machine faults, in accordance with an embodiment. Apparatus 800 can comprise a plurality of modules which may communicate with one another via a wired or wireless communication channel. Apparatus 800 may be realized using one or more integrated circuits, and may include fewer or more modules than those shown in FIG. 8. Further, apparatus 800 may be integrated in a computer system, or realized as a separate device which is capable of communicating with other computer systems and/or devices.

Specifically, apparatus 800 can comprise a sensor data receiver 802, a control signal data receiver 804, a feature generator 806, a classifier generator 808, and a fault detector 810. Note that apparatus 800 may also include additional modules and data not depicted in FIG. 8, and different implementations may arrange functionality according to a different set of modules. Embodiments of the present invention are not limited to any particular arrangement of modules.

Sensor data receiver 802 may receive a continuous stream of sensor data from a sensor. The sensor data indicates a condition of a machine, such as a measure of the temperature or pressure of a machine. Control data signal data receiver 804 may receive control signals from an agent, and the agent may obtain the control signals through an adapter connected to the machine. Feature generator 806 may analyze the control signal data to determine consistent intervals and aggregate time intervals, and segmentize corresponding sensor data to generate features. Classifier generator 808 may generate a classifier based on the generated features. Fault detector 810 may apply the generated classifier to sensor data to detect machine faults. Fault detector 810 may utilize feature generator 806 to generate features from sensor data and control signal input so that the classifier can classify sensor data segments under the same control signal conditions and/or other conditions that the classifier is trained with.

Figure 9:
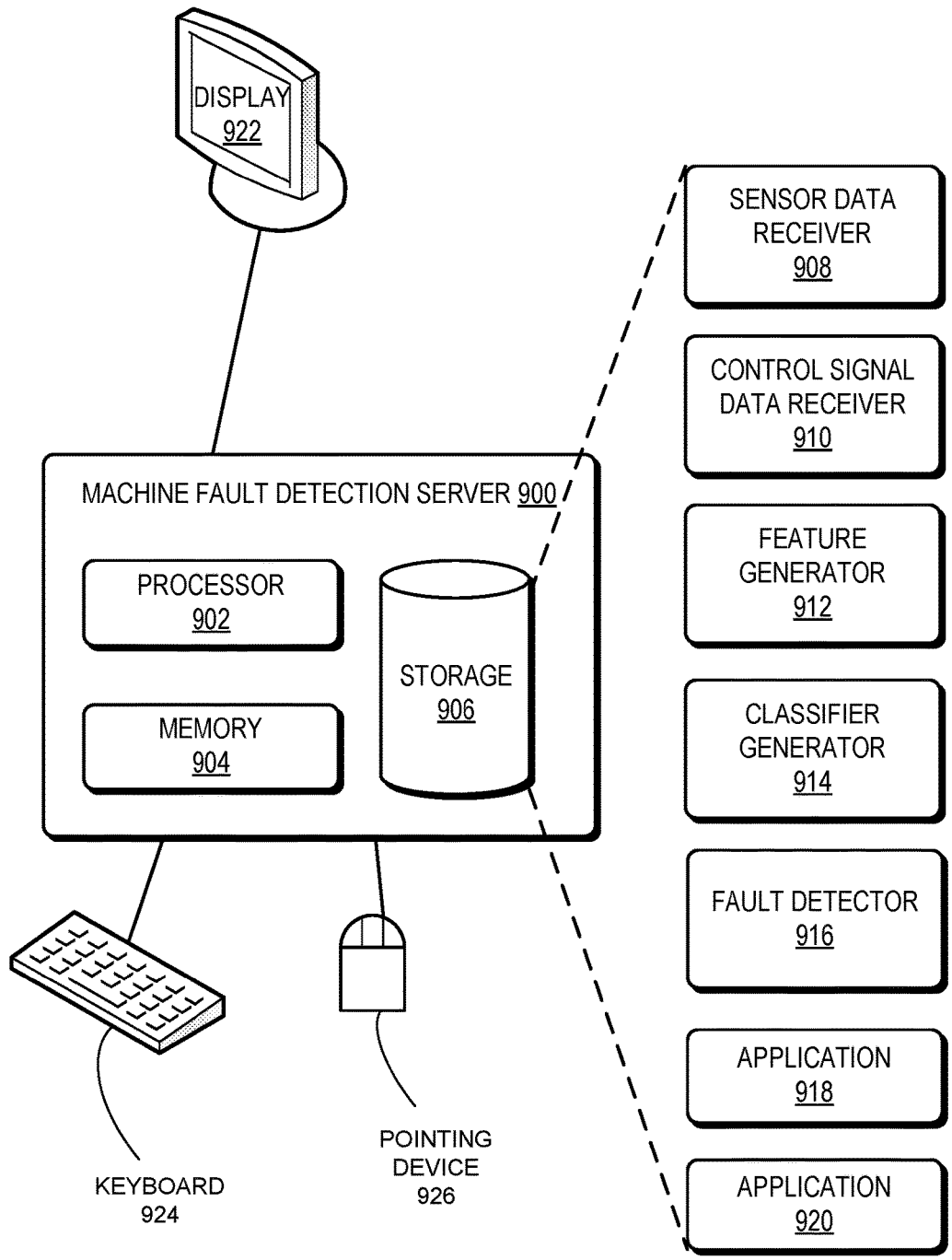
FIG. 9 presents an exemplary server in a machine fault detection system, in accordance with an embodiment of the present invention.

FIG. 9 presents a machine fault detection server 900 in a machine fault detection system, in accordance with an embodiment of the present invention. In FIG. 9, server 900 includes a processor 902, a memory 904, and a storage device 906. Storage device 906 stores programs to be executed by processor 902. Specifically, storage device 906 stores a sensor data receiver 908, a control signal data receiver 910, a feature generator 912, a classifier generator 914, and a fault detector 916, as well as other applications, such as applications 918 and 920. Machine fault detection server 900 may be coupled to an optional display 922, a keyboard 924, and a pointing device 926.

Sensor data receiver 908 may receive a continuous stream of sensor data from a sensor. The sensor data indicates a condition of a machine, such as a measure of the temperature or pressure of a machine. Control signal data receiver 910 may receive control signals from an agent, and the agent obtains the control signals through an adapter connected to the machine. Feature generator 912 may analyze the control signal data to determine consistent intervals and aggregate time intervals, and segmentize corresponding sensor data to generate features. Classifier generator 914 may generate a classifier based on the generated features. Fault detector 916 may apply the generated classifier to sensor data and control signal input (e.g., in the form of temporal segments) in order to detect machine faults. In some embodiments, fault detector 916 may utilize feature generator 912 to generate features from sensor data and control signal input so that the classifier can classify sensor data segments under the same control signal conditions and/or other conditions that the classifier is trained with.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium.

Furthermore, the methods and processes described below can be included in hardware modules. For example, the hardware modules can include, but are not limited to, application-specific integrated circuit (ASIC) chips, field-programmable gate arrays (FPGAs), and other programmable-logic devices now known or later developed. When the hardware modules are activated, the hardware modules perform the methods and processes included within the hardware modules.

The foregoing descriptions of embodiments of the present invention have been presented for purposes of illustration and description only. They are not intended to be exhaustive or to limit the present invention to the forms disclosed. Accordingly, many modifications and variations will be apparent to practitioners skilled in the art. Additionally, the above disclosure is not intended to limit the present invention. The scope of the present invention is defined by the appended claims.

What is claimed is:

1. A computer-executable method for detecting fault in a machine, comprising:
    obtaining a control signal associated with controlling the machine and sensor data that indicates a condition of the machine during a time period when the control signal controls the machine;
    determining consistent time intervals for the control signal, wherein during a consistent time interval the standard a standard deviation of the control signal is less than a predetermined threshold;

mapping the consistent time intervals to the sensor data to determine a plurality of time interval segments for the sensor data;
generating a plurality of training features based on the sensor data, wherein each respective feature is generated in association with from a time interval segment;
providing the plurality of training features as input to a classifier to train the classifier to classify abnormal sensor data during a respective consistent time interval;
generating new features for the classifier with same conditions as in classifier training by determining time intervals of a primary control signal that have same values for the primary control signal as a value of the primary control signal when generating the training features; and
detecting a machine fault by providing new features associated with additional machine sensor data as input to the classifier to detect abnormal sensor data during a respective consistent time interval.

2. The method of claim 1, wherein the control signal is at least one of a spindle motor speed, spindle load, and actual spindle speed; and wherein the sensor data is temperature data indicating a temperature associated with the machine.

3. The method of claim 1, wherein generating the plurality of training features includes computing at least one of an average, a standard deviation, a maximum fast Fourier transform (FFT) value, and a FFT frequency at maximum amplitude for the sensor data.

4. The method of claim 3, wherein the generated training features form a high-dimensional feature space, further comprising:
applying principal component analysis (PCA) to project the high-dimensional feature space into a low-dimensional space; and
applying linear discriminant analysis (LDA) to determine an optimal coordinate transformation that provides maximum separation between classes.

5. The method of claim 1, wherein determining consistent time intervals further comprises generating a temporal segment representation of the machine's operation context.

6. The method of claim 1, further comprising:
removing one or more control signal intervals that are inconsistent from a plurality of control signals before determining aggregate consistent intervals based on the plurality of control signals.

7. A non-transitory computer-readable storage medium storing instructions which when executed by a computer cause the computer to perform a method for detecting fault in a machine, the method comprising:
obtaining a control signal associated with controlling the machine and sensor data that indicates a condition of the machine during a time period when the control signal controls the machine;
determining consistent time intervals for the control signal, wherein during a consistent time interval a standard deviation of the control signal is less than a predetermined threshold;
mapping the consistent time intervals to the sensor data to determine a plurality of time interval segments for the sensor data;
generating a plurality of training features based on the sensor data, wherein each respective feature is generated in association with a time interval segment;
providing the plurality of training features as input to a classifier to train the classifier to classify abnormal sensor data during a respective consistent time interval;
generating new features for the classifier with same conditions as in classifier training by determining time intervals of a primary control signal that have same values for the primary control signal as a value of the primary control signal when generating the training features; and
detecting a machine fault by providing new features associated with additional machine sensor data as input to the classifier to detect abnormal sensor data during a respective consistent time interval.

8. The storage medium of claim 7, wherein the control signal is at least one of a spindle motor speed, spindle load, and actual spindle speed; and the and wherein the sensor data is temperature data indicating a temperature associated with the machine.

9. The storage medium of claim 7, wherein generating the plurality of training features includes computing at least one of an average, a standard deviation, a maximum fast Fourier transform (FFT) value, and a FFT frequency at maximum amplitude for the sensor data.

10. The storage medium of claim 7, wherein determining consistent time intervals further comprises generating a temporal segment representation of the machine's operation context.

11. The storage medium of claim 7, wherein the method further comprises:
removing one or more control signal intervals that are inconsistent from a plurality of control signals before determining aggregate consistent intervals based on the plurality of control signals.

12. A computing system comprising:
one or more processors;
a memory; and
a non-transitory computer-readable medium coupled to the one or more processors storing instructions stored that, when executed by the one or more processors, cause the computing system to perform a method comprising:
obtaining a control signal associated with controlling the machine and sensor data that indicates a condition of the machine during a time period when the control signal controls the machine;
determining consistent time intervals for the control signal, wherein during a consistent time interval a standard deviation of the control signal is less than a predetermined threshold;
mapping the consistent time intervals to the sensor data to determine a plurality of time interval segments for the sensor data;
generating a plurality of training features based on the sensor data, wherein each respective feature is generated in association with from a time interval segment;
providing the plurality of training features as input to a classifier to train the classifier to classify abnormal sensor data during a respective consistent time interval;
generating new features for the classifier with same conditions as in classifier training by determining time intervals of a primary control signal that have same values for the primary control signal as a value of the primary control signal when generating the training features; and
detecting a machine fault by providing new features associated with additional machine sensor data as input to the classifier to detect abnormal sensor data during a respective consistent time interval.

13. The computing system of claim 12, wherein the control signal is at least one of a spindle motor speed, spindle load, and actual spindle speed; and wherein the sensor data is temperature data indicating a temperature associated with the machine.

14. The computing system of claim 12, wherein generating the plurality of training features includes computing at least one of an average, a standard deviation, a maximum fast Fourier transform (FFT) value, and a FFT frequency at maximum amplitude for the sensor data.

15. The method of claim 1, further comprising:
aggregating consistent time intervals of a plurality of control signals to determine aggregate consistent intervals.

16. The method of claim 15, wherein aggregating the consistent time intervals comprises determining an intersection of sets of consistent time intervals over all control signals.

17. The storage medium of claim 7, wherein the method further comprises:
aggregating consistent time intervals of a plurality of control signals to determine aggregate consistent intervals.

18. The storage medium of claim 17, wherein aggregating the consistent time intervals comprises determining an intersection of sets of consistent time intervals over all control signals.

19. The computing system of claim 12, wherein the method further comprises:
aggregating consistent time intervals of a plurality of control signals to determine aggregate consistent intervals.

20. The computing system of claim 19, wherein aggregating the consistent time intervals comprises determining an intersection of sets of consistent time intervals over all control signals.

* * * * *